(12) United States Patent
Kawamura

(10) Patent No.: US 12,064,278 B2
(45) Date of Patent: Aug. 20, 2024

(54) LEARNING DEVICE, LEARNING METHOD, AND LEARNING PROGRAM, RADIATION IMAGE PROCESSING DEVICE, RADIATION IMAGE PROCESSING METHOD, AND RADIATION IMAGE PROCESSING PROGRAM

(71) Applicant: FUJIFILM Corporation, Tokyo (JP)

(72) Inventor: Takahiro Kawamura, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 277 days.

(21) Appl. No.: 17/707,724

(22) Filed: Mar. 29, 2022

(65) Prior Publication Data

US 2022/0323032 A1 Oct. 13, 2022

(30) Foreign Application Priority Data

Apr. 2, 2021 (JP) .................................. 2021-063571

(51) Int. Cl.
*A61B 6/50* (2024.01)
*A61B 6/04* (2006.01)
(Continued)

(52) U.S. Cl.
CPC ............ *A61B 6/505* (2013.01); *A61B 6/0407* (2013.01); *A61B 6/4291* (2013.01); *G06N 3/08* (2013.01)

(58) Field of Classification Search
CPC ..... A61B 6/0407; A61B 6/4291; A61B 6/482; A61B 6/505; A61B 6/5217; A61B 6/582;
(Continued)

(56) References Cited

U.S. PATENT DOCUMENTS

| 6,269,351 | B1 * | 7/2001 | Black | .................... | G06F 16/30 706/14 |
| 2011/0305405 | A1 * | 12/2011 | Kawamura | ............... | G06T 3/14 382/294 |

(Continued)

FOREIGN PATENT DOCUMENTS

| JP | 2011-255060 A | 12/2011 |
| JP | 2015-043959 A | 3/2015 |
| JP | 2018-153605 A | 10/2018 |

*Primary Examiner* — Dani Fox
*Assistant Examiner* — Soorena Kefayati
(74) *Attorney, Agent, or Firm* — Studebaker & Brackett PC

(57) ABSTRACT

By subjecting a neural network to machine learning using teacher data consisting of learning data and correct answer data, a trained neural network that outputs at least one of a composition of a target subject or a body thickness of the target subject in a case in which at least one target radiation image of the target subject is input is constructed. The learning data includes a standard image acquired by irradiating a standard object of which a thickness and a material are known with radiation in a state in which an object is interposed between the standard object and a radiation detector, an energy characteristic of the radiation, a thickness and a material of the object, and an imaging condition in a case in which the standard image is acquired. The correct answer data includes at least one of a composition or a body thickness of a subject derived from at least one radiation image of the subject by using the standard image, the energy characteristic of the radiation, the thickness and the material of the object, and the imaging condition.

13 Claims, 17 Drawing Sheets

(51) Int. Cl.
  *A61B 6/42* (2024.01)
  *G06N 3/08* (2023.01)
(58) Field of Classification Search
  CPC ..... A61B 6/583; A61B 6/5252; A61B 6/5258;
       A61B 6/5282; A61B 6/5294; G06N 3/08;
       G06N 3/0464; G06N 3/084; G06N 3/09
  See application file for complete search history.

(56) References Cited

U.S. PATENT DOCUMENTS

| | | | |
|---|---|---|---|
| 2012/0014584 A1* | 1/2012 | Han | A61B 6/50 |
| | | | 382/132 |
| 2012/0148156 A1* | 6/2012 | Sehnert | A61B 6/4291 |
| | | | 345/581 |
| 2015/0371378 A1* | 12/2015 | Schmidt | G06F 18/2193 |
| | | | 382/131 |
| 2016/0140720 A1* | 5/2016 | Naito | A61B 6/5211 |
| | | | 382/132 |
| 2018/0122094 A1 | 5/2018 | Naito | |
| 2018/0263559 A1* | 9/2018 | Kawamura | A61B 6/032 |
| 2018/0368731 A1* | 12/2018 | Oh | G16H 40/63 |
| 2019/0021677 A1* | 1/2019 | Grbic | G06T 7/11 |
| 2020/0281543 A1* | 9/2020 | Sahbaee Bagherzadeh | |
| | | | A61B 6/032 |
| 2020/0367844 A1* | 11/2020 | Dang | G06T 5/60 |
| 2021/0161487 A1* | 6/2021 | Chen | G06T 7/0012 |
| 2021/0267563 A1* | 9/2021 | Sattarivand | A61B 6/505 |

* cited by examiner

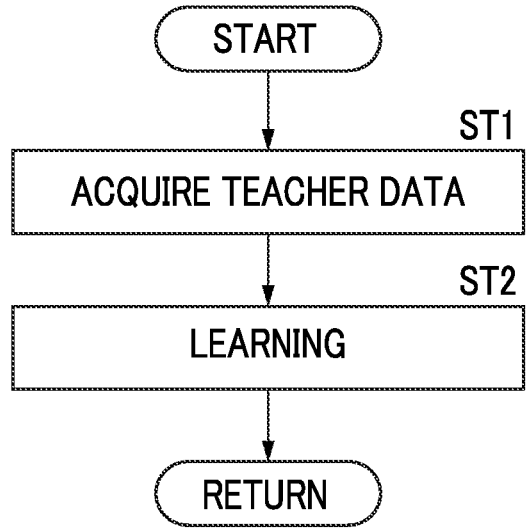
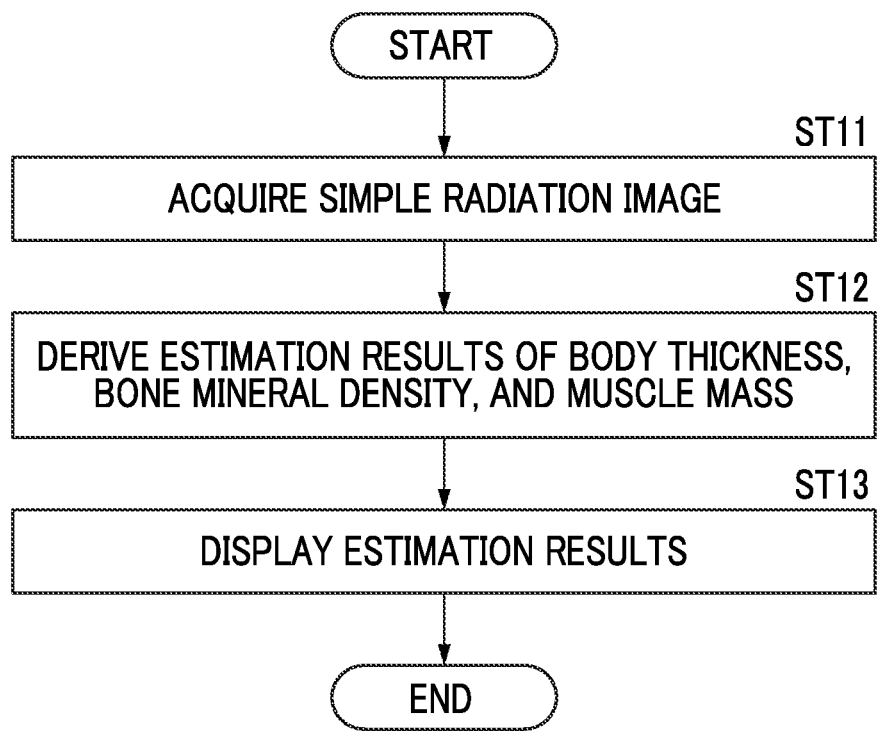

LEARNING DEVICE, LEARNING METHOD, AND LEARNING PROGRAM, RADIATION IMAGE PROCESSING DEVICE, RADIATION IMAGE PROCESSING METHOD, AND RADIATION IMAGE PROCESSING PROGRAM

CROSS REFERENCE TO RELATED APPLICATIONS

The present application claims priority under 35 U.S.C. § 119 to Japanese Patent Application No. 2021-063571 filed on Apr. 2, 2021. The above application is hereby expressly incorporated by reference, in its entirety, into the present application.

BACKGROUND

Technical Field

The present disclosure relates to a learning device, a learning method, a learning program, a radiation image processing device, a radiation image processing method, and a radiation image processing program.

Related Art

In the related art, energy subtraction processing using two radiation images obtained by irradiating a subject with two types of the radiation having different energy distributions by using an amount of attenuation of transmitted radiation different from each other depending on a substance configuring the subject is known. The energy subtraction processing is a method in which pixels of the two radiation images obtained as described above are associated with each other, and the pixels are multiplied by an appropriate weighting coefficient and then subtracted (subtract) to acquire an image obtained by extracting a specific structure included in the radiation image. By performing such energy subtraction processing, for example, in a case in which a soft part image obtained by extracting a soft part from the radiation image acquired by imaging a chest is derived, a shadow appearing on the soft part can be observed without being disturbed by a bone. On the contrary, in a case in which a bone part image obtained by extracting the bone part is derived, the shadow appearing on a bone part can be observed without being disturbed by the soft part.

In addition, various methods for deriving a composition of a human body, such as a bone mineral density, a fat, and a muscle, by the energy subtraction processing have also been proposed. For example, JP2018-153605A proposes a method in which a soft part image obtained by extracting a soft part of a subject is generated from a plurality of radiation images acquired by radiation having different energy distributions transmitted through the subject, a body thickness distribution of the subject is estimated based on an imaging condition in a case in which the soft part image and the radiation image are acquired, an approximate body thickness distribution that approximates the estimated body thickness distribution with a model corresponding to a human body is calculated, and a distribution of a body fat percentage in the subject is calculated based on the approximate body thickness distribution.

On the other hand, in a case of imaging the radiation image of the subject, particularly in a case in which the thickness of the subject is large, there is a problem that the radiation is scattered in the subject to generate scattered rays, and the contrast of the acquired radiation image is lowered by the generated scattered rays. Therefore, scattered ray removal processing for removing a scattered ray component included in the radiation image is performed (see, for example, JP2015-043959A). With the method disclosed in JP2015-043959A, the scattered ray removal processing is performed by deriving the scattered ray component of the radiation image based on a radiation attenuation coefficient of the subject, and subtracting the derived scattered ray component from the radiation image. By applying such scattered ray removal processing in a case of performing the energy subtraction processing, it is possible to acquire the bone part image and the soft part image in which the composition is separated with higher accuracy.

By the way, in a case in which radiation imaging of the subject is actually performed, a grid may be used between the subject and a radiation detector, or an object, such as an imaging table or a top plate of the imaging table may be interposed. Since such an object has a peculiar radiation characteristic, the radiation attenuation coefficient is changed due to beam hardening, which hardens a radiation quality by being transmitted through the object. Specifically, the beam hardening reduces the radiation attenuation coefficient. In addition, the radiation attenuation coefficient is smaller as the energy of the radiation emitted to the subject is higher. Therefore, the composition of the subject and the body thickness cannot be estimated with high accuracy unless an energy characteristic of the radiation and the radiation characteristic of the object interposed between the subject and the radiation detector are taken into consideration.

SUMMARY OF THE INVENTION

The present disclosure has been made in view of the above circumstances, and is to estimate at least one of a body thickness or a composition of a subject with high accuracy.

The present disclosure relates to a learning device comprising at least one processor, in which the processor constructs, by subjecting a neural network to machine learning using teacher data consisting of learning data and correct answer data, a trained neural network that outputs at least one of a composition of a target subject or a body thickness of the target subject in a case in which at least one target radiation image of the target subject is input, the learning data includes a standard image acquired by irradiating a standard object of which a thickness and a material are known with radiation in a state in which an object is interposed between the standard object and a radiation detector, an energy characteristic of the radiation, a thickness and a material of the object, and an imaging condition in a case in which the standard image is acquired, and the correct answer data includes at least one of a composition or a body thickness of a subject derived from at least one radiation image of the subject by using the standard image, the energy characteristic of the radiation, the thickness and the material of the object, and the imaging condition.

Note that, in the learning device according to the present disclosure, the object may be at least one of a top plate of an imaging table on which a subject is placed in an imaging apparatus or a scattered ray removal grid for removing a scattered ray component from radiation transmitted through the subject.

In addition, in the learning device according to the present disclosure, the target radiation image may be a simple radiation image based on radiation transmitted through the target subject including a bone part and a soft part.

In addition, in the learning device according to the present disclosure, the target radiation image may be a first radiation image and a second radiation image based on radiation having different energy distributions transmitted through the target subject including a bone part and a soft part.

In addition, in the learning device according to the present disclosure, the composition of the subject and the composition of the target subject may be at least one of a bone mineral density or a muscle mass.

The present disclosure relates to a radiation image processing device comprising at least one processor, in which the processor acquires at least one target radiation image of a target subject, and derives an estimation result of at least one of a composition of the target subject or a body thickness of the target subject by using a trained neural network constructed by the learning device according to the present disclosure, and the target radiation image.

Note that, in the radiation image processing device according to the present disclosure, the target radiation image may be a simple radiation image based on radiation transmitted through the target subject including a bone part and a soft part.

In addition, in the radiation image processing device according to the present disclosure, the target radiation image may be a first radiation image and a second radiation image based on radiation having different energy distributions transmitted through the target subject including a bone part and a soft part.

In addition, in the radiation image processing device according to the present disclosure, the composition of the target subject may be at least one of a bone mineral density or a muscle mass.

The present disclosure relates to a learning method of constructing, by subjecting a neural network to machine learning using teacher data consisting of learning data and correct answer data, a trained neural network that outputs at least one of a composition of a target subject or a body thickness of the target subject in a case in which at least one target radiation image of the target subject is input, in which the learning data includes a standard image acquired by irradiating a standard object of which a thickness and a material are known with radiation in a state in which an object is interposed between the standard object and a radiation detector, an energy characteristic of the radiation, a thickness and a material of the object, and an imaging condition in a case in which the standard image is acquired, and the correct answer data includes at least one of a composition or a body thickness of a subject derived from at least one radiation image of the subject by using the standard image, the energy characteristic of the radiation, the thickness and the material of the object, and the imaging condition.

The present disclosure relates to a radiation image processing method comprising acquiring at least one target radiation image of a target subject, and deriving an estimation result of at least one of a composition of the target subject or a body thickness of the target subject by using a trained neural network constructed by the learning device according to the present disclosure, and the target radiation image.

Note that the learning method and the radiation image processing method according to the present disclosure may be provided as a program executed by a computer.

According to the present disclosure, it is possible to estimate at least one of the body thickness or the composition of the subject with high accuracy.

BRIEF DESCRIPTION OF THE DRAWINGS

FIG. 20 is a flowchart of learning processing performed in the present embodiment.

FIG. 21 is a flowchart of radiation image processing performed in the present embodiment.

DETAILED DESCRIPTION

Figure 1:
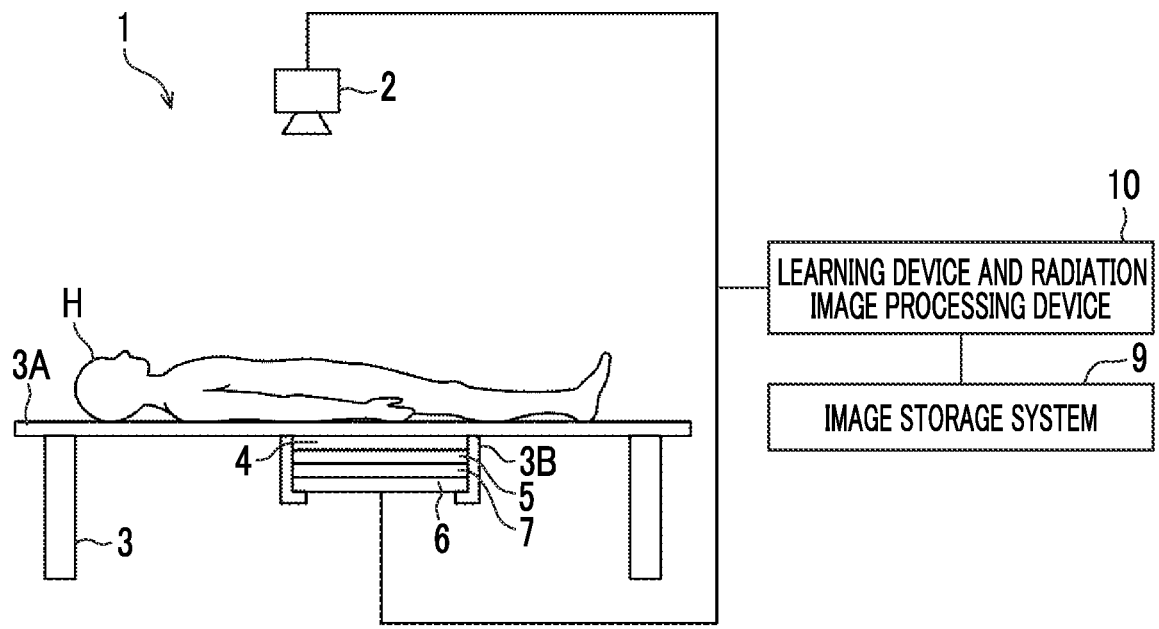
FIG. 1 is a schematic block diagram showing a configuration of a radiography system to which a learning device and a radiation image processing device according to an embodiment of the present disclosure are applied.

In the following, an embodiment of the present disclosure will be described with reference to the drawings. FIG. 1 is a schematic block diagram showing a configuration of a radiography system to which a learning device and a radiation image processing device according to the embodiment of the present disclosure are applied. As shown in FIG. 1, the radiography system according to the present embodiment comprises an imaging apparatus 1, a learning device and radiation image processing device (hereinafter may be represented by the radiation image processing device) 10 according to the present embodiment.

The imaging apparatus 1 is an imaging apparatus that can perform energy subtraction by a so-called one-shot method of converting radiation, such as X-rays, emitted from a radiation source 2 and transmitted through a subject H who lies on an imaging table 3 into energy and irradiating a first radiation detector 5 and a second radiation detector 6 with the converted radiation. At the time of imaging, as shown in FIG. 1, a scattered ray removal grid (hereinafter simply referred to as a grid) 4, the first radiation detector 5, a radiation energy conversion filter 7 made of a copper plate or the like, and the second radiation detector 6 are disposed in order from a side closest to the radiation source 2, and the radiation source 2 is driven. The first and second radiation detectors 5 and 6 are closely attached to the radiation energy conversion filter 7. Note that the grid 4, the first radiation detector 5, the radiation energy conversion filter 7, and the second radiation detector 6 are attachably and detachably attached below the top plate 3A of the imaging table 3 by an attachment portion 3B.

As a result, in the first radiation detector 5, a first radiation image G1 of the subject H by low-energy radiation including so-called soft rays is acquired. In addition, in the second radiation detector 6, a second radiation image G2 of the subject H by high-energy radiation from which the soft rays are removed is acquired. Therefore, the first and second radiation images G1 and G2 are the radiation images having different energy distributions. The first and second radiation images G1 and G2 are input to the radiation image processing device 10.

The first and second radiation detectors 5 and 6 can perform recording and reading-out of the radiation image repeatedly. A so-called direct-type radiation detector that directly receives emission of the radiation and generates an electric charge may be used, or a so-called indirect-type radiation detector that converts the radiation into visible light and then converts the visible light into an electric charge signal may be used. In addition, as a method for reading out a radiation image signal, it is desirable to use a so-called thin film transistor (TFT) readout method in which the radiation image signal is read out by turning a TFT switch on and off, or a so-called optical readout method in which the radiation image signal is read out by emission of read out light. However, other methods may also be used without being limited to these methods.

Note that, in the present embodiment, in the imaging apparatus 1, only one radiation detector may be attached to the attachment portion 3B to image the subject H. The imaging in this case is referred to as simple imaging, and the radiation image acquired by the simple imaging is referred to as a simple radiation image G0.

The grid 4 is configured by lead that does not transmit the radiation and an interspace material, such as aluminum or fiber that easily transmit the radiation which are disposed alternately with a fine grid density of about 4.0 lines/mm. By using the grid 4, a scattered ray component of the radiation transmitted through the subject H can be removed, but it cannot be completely removed. Therefore, the first and second radiation images G1 and G2 or the simple radiation image G0 include a primary ray component of the radiation transmitted through the subject H as well as the scattered ray component.

Note that the primary ray component is a signal component having a pixel value represented by the radiation that reaches the radiation detector without being scattered by the subject H in the radiation that is transmitted through the subject H. On the other hand, the scattered ray component is a signal component having a pixel value represented by the radiation that reaches the radiation detector by being scattered by the subject H in the radiation that is transmitted through the subject H.

The radiation image processing device 10 is connected to an image storage system 9 via a network (not shown). The image storage system 9 is a system that stores image data of the radiation image captured by the imaging apparatus 1. The image storage system 9 extracts an image corresponding to a request from the radiation image processing device 10 from the stored radiation image and transmits the extracted image to a request source device. Specific examples of the image storage system 9 include picture archiving and communication systems (PACS).

Figure 2:
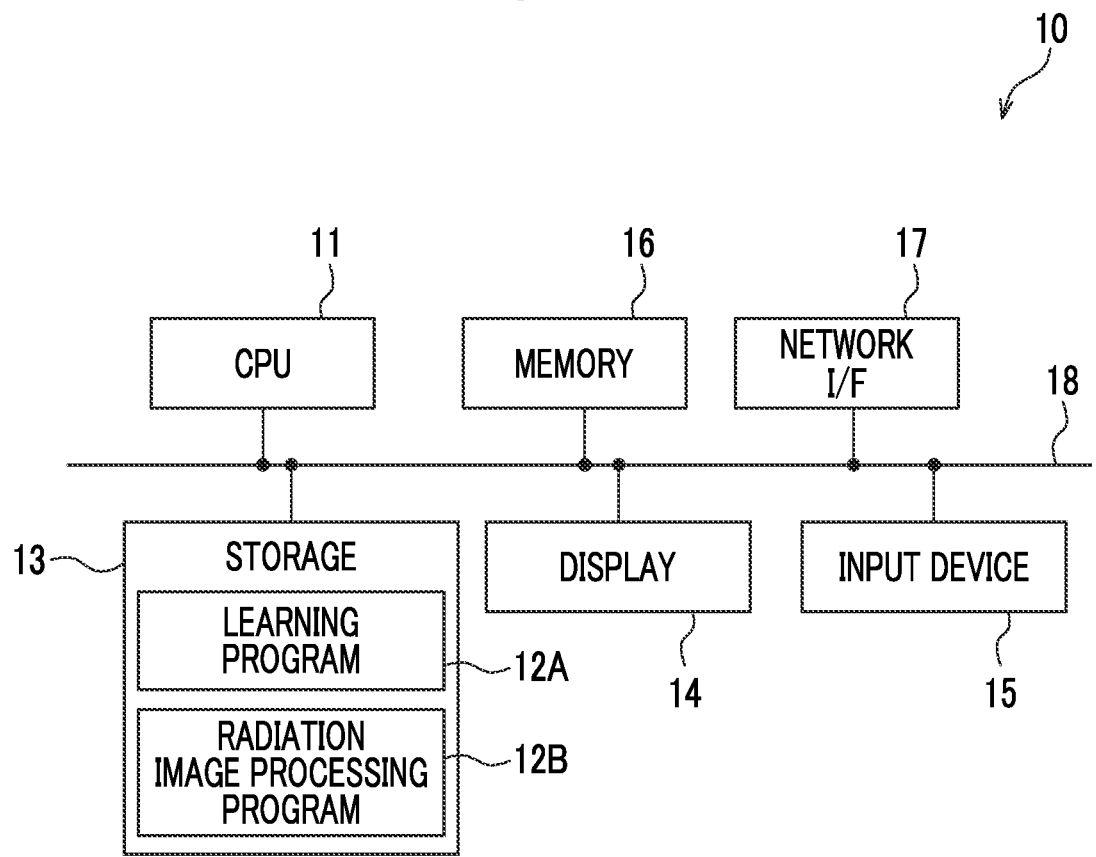
FIG. 2 is a diagram showing a schematic configuration of the learning device and the radiation image processing device according to the present embodiment.

Then, the learning device and the radiation image processing device according to the present embodiment will be described. First, with reference to FIG. 2, a hardware configuration of the learning device and the radiation image processing device according to the present embodiment will be described. As shown in FIG. 2, the radiation image processing device 10 is a computer, such as a workstation, a server computer, and a personal computer, and comprises a central processing unit (CPU) 11, a non-volatile storage 13, and a memory 16 as a transitory storage region. In addition, the learning device and radiation image processing device 10 comprise a display 14, such as a liquid crystal display, an input device 15, such as a keyboard and a mouse, and a network interface (I/F) 17 connected to a network (not shown). The CPU 11, the storage 13, the display 14, the input device 15, the memory 16, and the network T/F 17 are connected to a bus 18. Note that the CPU 11 is an example of a processor according to the present disclosure.

The storage 13 is realized by a hard disk drive (HDD), a solid state drive (SSD), a flash memory, and the like. The storage 13 as a storage medium stores a learning program 12A and a radiation image processing program 12B installed in the learning device and radiation image processing device 10. The CPU 11 reads out the learning program 12A and the radiation image processing program 12B from the storage 13 and expands the read out learning program 12A and radiation image processing program 12B in the memory 16, and executes the expanded learning program 12A and radiation image processing program 12B.

Note that the learning program 12A and the radiation image processing program 12B are stored in a storage device of the server computer connected to the network or in a network storage in a state of being accessible from the outside, and are downloaded and installed in the computer that configures the learning device and radiation image processing device 10 in response to the request. Alternatively, the learning program 12A and the radiation image processing program 12B are distributed in a state of being recorded on a recording medium, such as a digital versatile disc (DVD) or a compact disc read only memory (CD-ROM), and are installed in the computer that configures the learning device and radiation image processing device 10 from the recording medium.

Figure 3:
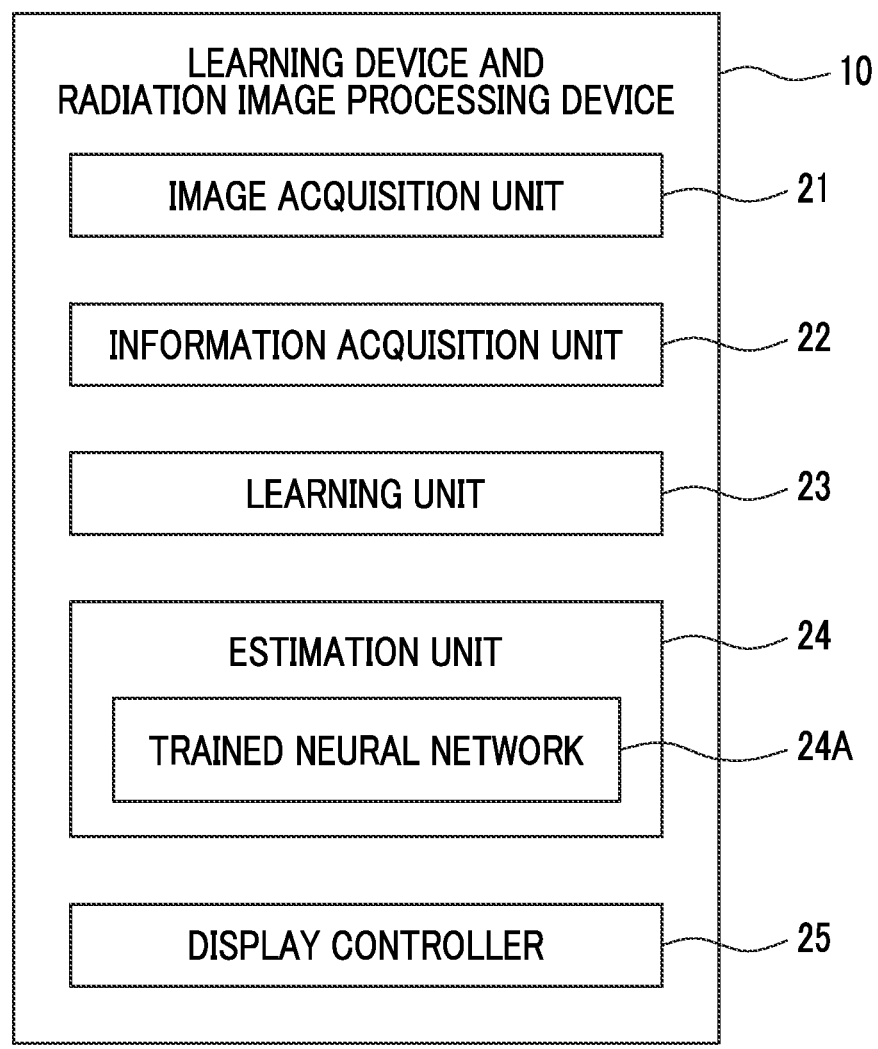
FIG. 3 is a diagram showing a functional configuration of the learning device and the radiation image processing device according to the present embodiment.

Then, a functional configuration of the learning device and the radiation image processing device according to the present embodiment will be described. FIG. 3 is a diagram showing the functional configuration of the learning device and the radiation image processing device according to the present embodiment. As shown in FIG. 3, the learning device and radiation image processing device 10 comprises an image acquisition unit 21, an information acquisition unit 22, a learning unit 23, an estimation unit 24, and a display controller 25. Moreover, the CPU 11 functions as the information acquisition unit 22 and the learning unit 23 by executing the learning program 12A. In addition, the CPU 11 functions as the image acquisition unit 21, the estimation unit 24, and the display controller 25 by executing the radiation image processing program 12B.

In a case in which the estimation results of the body thickness, the bone mineral density, and the muscle mass of the subject H, which is a target, are derived in the radiation image processing device 10, the image acquisition unit 21 acquires the simple radiation image G0 of the subject H from the first radiation detector 5 by causing the imaging apparatus 1 to perform simple imaging of the subject H. Note that the image acquisition unit 21 may acquire the first radiation image G1 and the second radiation image G2 having different energy distributions for the subject H from the first and second radiation detectors 5 and 6 by causing the imaging apparatus 1 to image the subject H. In a case in which the simple radiation image G0, the first radiation image G1 and the second radiation image G2 are acquired, the imaging condition, such as an imaging dose, a tube voltage, a source image receptor distance (SID) which is a distance between the radiation source 2 and surfaces of the first and second radiation detectors 5 and 6, a source object distance (SOD) which is a distance between the radiation source 2 and a surface of the subject H, and the presence or absence of a scattered ray removal grid are set.

The SOD and the SID are used to calculate a body thickness distribution as described below. It is preferable that the SOD be acquired by, for example, a time of flight (TOF) camera. It is preferable that the SID be acquired by, for example, a potentiometer, an ultrasound range finder, a laser range finder, or the like.

The imaging condition need only be set by input from the input device 15 by an operator. The set imaging condition is stored in the storage 13. Note that, in the present embodiment, the simple radiation image G0, or the first and second radiation images G1 and G2 may be acquired by a program separate from the radiation image processing program 12B and stored in the storage 13. In this case, the image acquisition unit 21 acquires the simple radiation image G0, or the first and second radiation images G1 and G2 stored in the storage 13 by reading out the simple radiation image G0, or the first and second radiation images G1 and G2 from the storage 13 for processing.

The information acquisition unit 22 acquires the teacher data for learning a neural network, which will be described below, from the image storage system 9 via the network I/F 17. The teacher data will be described below.

By subjecting the neural network to machine learning using the teacher data acquired by the information acquisition unit 22, the learning unit 23 constructs a trained neural network 24A that outputs the body thickness, the bone mineral density, and the muscle mass of the subject H in a case in which the simple radiation image G0 of the subject H, which is a target, is input.

Examples of the neural network include a simple perceptron, a multi-layer perceptron, a deep neural network, a convolutional neural network, a deep belief network, a recurrent neural network, and a stochastic neural network. In the present embodiment, the convolutional neural network is used as the neural network.

Figure 4:
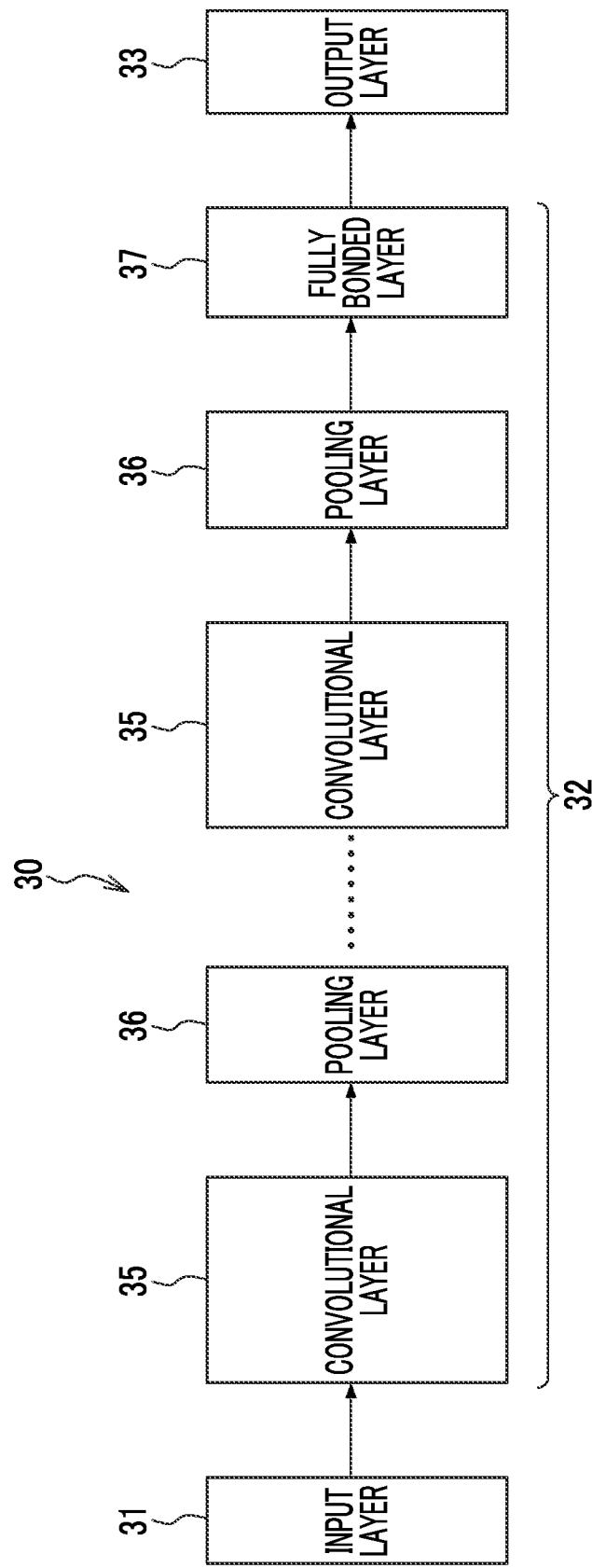
FIG. 4 is a diagram showing a schematic configuration of a neural network used in the present embodiment.

FIG. 4 is a diagram showing the neural network used in the present embodiment. As shown in FIG. 4, a neural network 30 comprises an input layer 31, an interlayer 32, and an output layer 33. The interlayer 32 comprises, for example, a plurality of convolutional layers 35, a plurality of pooling layers 36, and a fully bonded layer 37. In the neural network 30, the fully bonded layer 37 is present in front of the output layer 33. Moreover, in the neural network 30, the convolutional layer 35 and the pooling layer 36 are alternately disposed between the input layer 31 and the fully bonded layer 37.

Note that a configuration of the neural network 30 is not limited to the example of FIG. 4. For example, the neural network 30 may comprise one convolutional layer 35 and one pooling layer 36 between the input layer 31 and the fully bonded layer 37.

Figure 5:
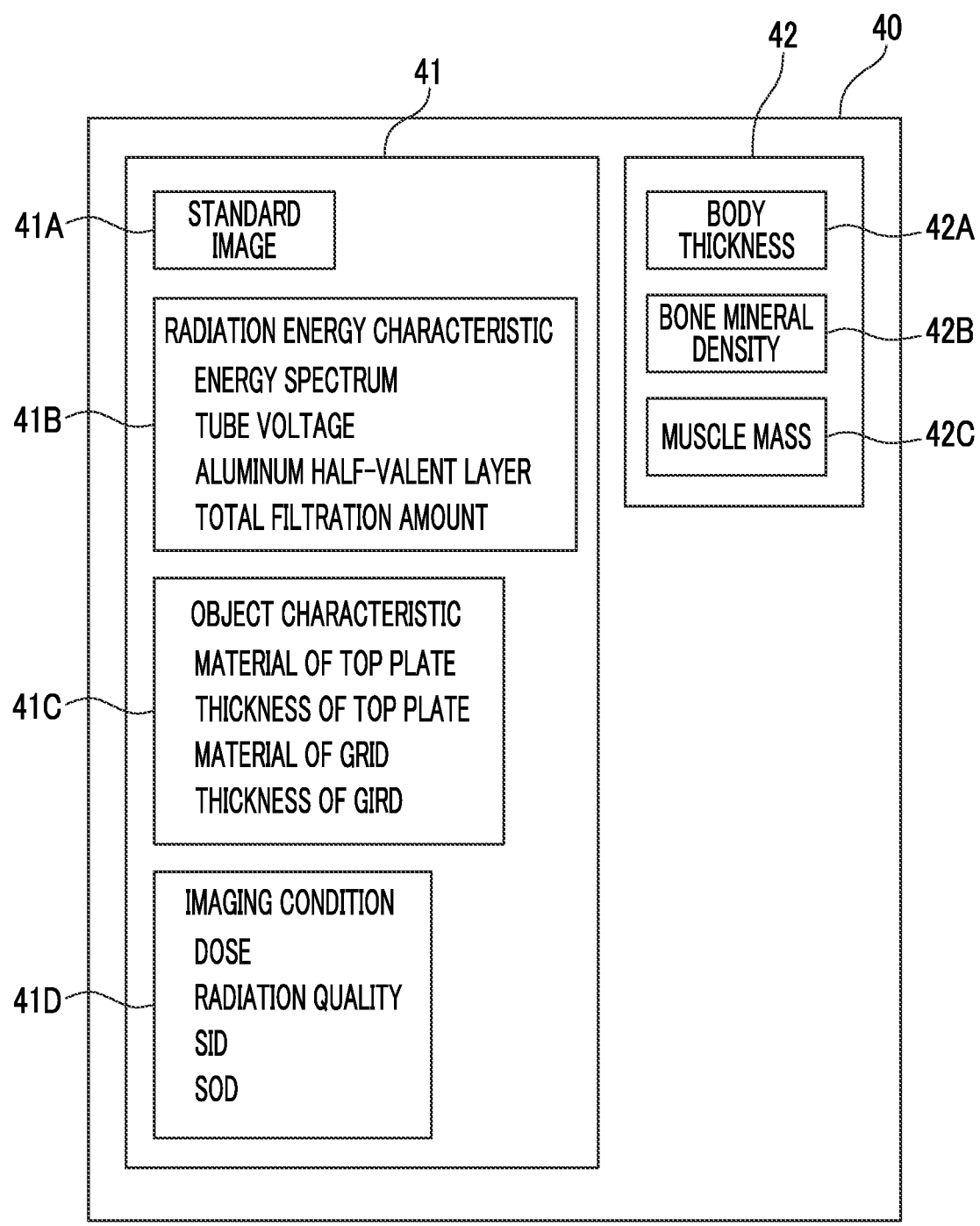
FIG. 5 is a diagram showing teacher data.

FIG. 5 is a diagram showing an example of the teacher data used for learning the neural network. As shown in FIG. 5, teacher data 40 consists of learning data 41 and correct answer data 42. The learning data 41 includes a standard image 41A, a radiation energy characteristic 41B, an object characteristic 41C, and an imaging condition 41D. The correct answer data 42 includes a body thickness 42A, a bone mineral density 42B, and a muscle mass 42C of a certain subject derived based on the radiation image of the subject. Note that the body thickness 42A, the bone mineral density 42B, and the muscle mass 42C are values obtained for each pixel of the radiation image.

The radiation energy characteristic 41B includes at least one of an energy spectrum of the radiation, a tube voltage, an aluminum half-valent layer, or a total filtration amount. The radiation energy characteristic 41B will be described below. The object characteristic 41C includes a material and a thickness of each of the top plate 3A and the grid 4, which are objects interposed between the subject H (or standard object described below) and the radiation detector 5. Examples of the material of the top plate 3A include acrylic. The material of the grid 4 is a material of the interspace material constituting the grid 4, and examples thereof include aluminum. The imaging condition 41D includes at least one of the dose, radiation quality, SID, or SOD at the time of imaging.

For the teacher data 40, a plurality of changed combinations of the thickness of the standard object, the radiation energy characteristic, the object characteristic, and the imaging condition as the learning data 41, and the body thickness, the bone mineral density, and the muscle mass as the correct answer data 42 are prepared. Note that the derivation of the correct answer data 42 included in the teacher data 40 will be described below.

Figure 6:
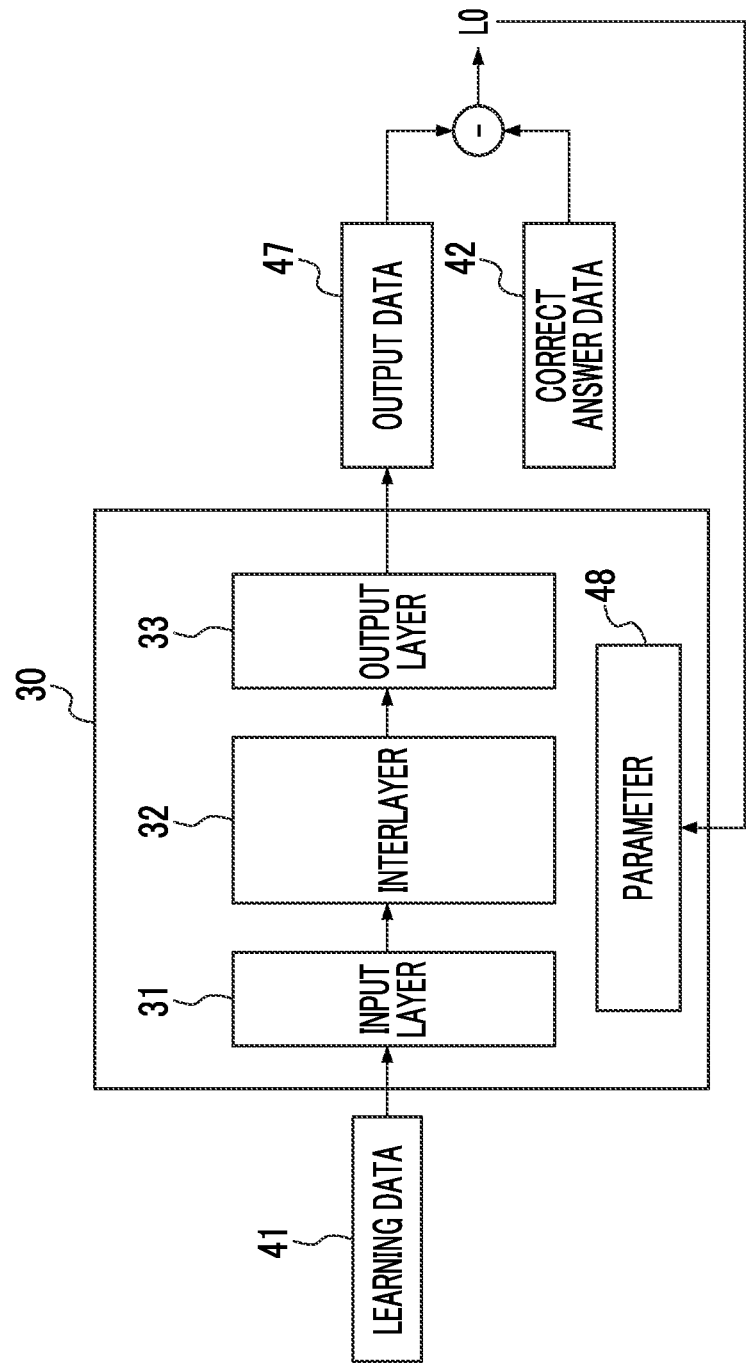
FIG. 6 is a diagram for describing learning of the neural network.

The learning unit 23 trains the neural network using a large amount of the teacher data 40. FIG. 6 is a diagram for describing learning of the neural network 30. In a case in which learning of the neural network 30 is performed, the learning unit 23 inputs the standard image 41A, the radiation energy characteristic 41B, the object characteristic 41C, and the imaging condition 41D which are the learning data 41 to the input layer 31 of the neural network 30.

Note that, for the standard image 41A, the pixel value of each pixel of the standard image 41A is input. In a case in which the radiation energy characteristic 41B is the energy spectrum, a relationship between the number of relative radiation photons with respect to the radiation energy (that is, a value of the number of relative radiation photons with respect to the radiation energy) is input. In a case in which the radiation energy characteristic 41B is the aluminum half-valent layer, the combination of the tube voltage and the aluminum half-valent layer is input. In a case in which the radiation energy characteristic 41B is the total filtration amount, the combination of the tube voltage and the total filtration amount is input. For the object characteristic 41C, the thickness and the material of the object, that is, the top plate 3A and the grid 4 are input. For the imaging condition 41D, the values of the dose, the radiation quality, the SID, and the SOD at the time of imaging are input, respectively.

Moreover, the learning unit 23 outputs the body thickness, the bone mineral density, and the muscle mass as output data 47 from the output layer 33 of the neural network 30.

Moreover, the learning unit 23 derives a difference between the output data 47 and the correct answer data 42 as a loss L0. Note that the loss L0 is the sum of differences between each of the body thickness, the bone mineral density, and the muscle mass included in the output data 47, and each of the body thickness 42A, the bone mineral density 42B, and the muscle mass 42C included in the correct answer data 42.

The learning unit 23 trains the neural network 30 based on the loss L0. Specifically, the learning unit 23 adjusts a kernel coefficient in the convolutional layer 35, a weight of the bond between the layers, a weight of the bond in the fully bonded layer 37, and the like (hereinafter referred to as a parameter 48) such that the loss L0 is reduced. For example, an error backpropagation method can be used as a method for adjusting the parameter 48. The learning unit 23 repeats the adjustment of the parameter 48 until a termination condition is satisfied. The termination condition is that the loss L0 is equal to or less than a predetermined threshold value, or that the learning is performed a predetermined number of times.

As a result, in a case in which the simple radiation image G0 of the subject H, which is a target, is input, the parameter 48 is adjusted to output the body thickness, the bone mineral density, and the muscle mass of the subject H in each pixel of the input simple radiation image G0, and the trained neural network 24A is constructed. The constructed trained neural network 24A is stored in the storage 13.

Figure 7:
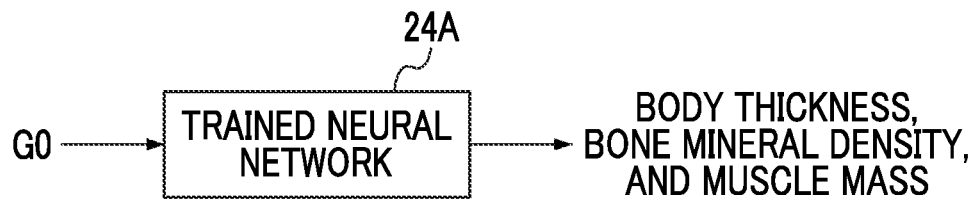
FIG. 7 is a conceptual diagram of processing performed by a trained neural network.

FIG. 7 is a conceptual diagram of processing performed by the trained neural network 24A. As shown in FIG. 7, in a case in which the simple radiation image G0 of the patient is input to the trained neural network 24A constructed as described above, the trained neural network 24A outputs the body thickness, the bone mineral density, and the muscle mass (that is, the body thickness distribution, the bone mineral density distribution, and the muscle mass distribution) for each pixel of the input simple radiation image G0.

The estimation unit 24 derives the estimation results of the body thickness, the bone mineral density, and the muscle mass of the subject H from the simple radiation image G0 acquired by imaging the subject H, which is a target. In the present embodiment, the estimation unit 24 derives the estimation results of the body thickness, the bone mineral density, and the muscle mass of the subject H by inputting the simple radiation image G0 to the trained neural network 24A and outputting the body thickness, the bone mineral density, and the muscle mass from the trained neural network 24A.

Figure 8:
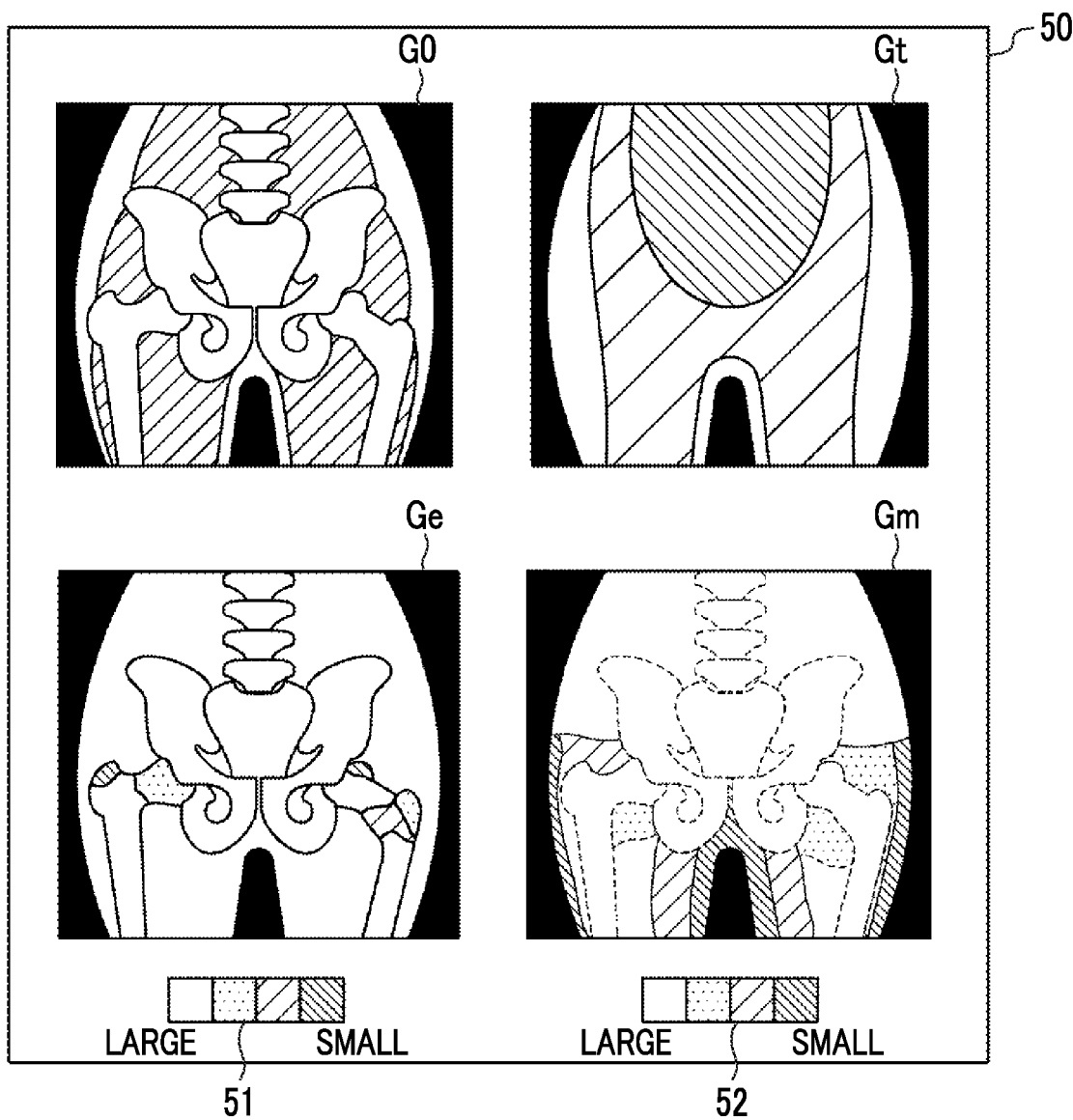
FIG. 8 is a diagram showing a display screen.

The display controller 25 displays the estimation results of the body thickness, the bone mineral density, and the muscle mass estimated by the estimation unit 24 on the display 14. FIG. 8 is a diagram showing a display screen of the estimation result. As shown in FIG. 8, on the display screen 50, the simple radiation image G0 of the subject H, a body thickness image Gt which is the estimation result of the body thickness, a bone mineral image Ge which is the estimation result of the bone mineral density, and a muscle image Gm which is the estimation result of the muscle mass are displayed. A pattern according to the body thickness is added to the body thickness image Gt. A pattern according to the bone mineral density distribution is added to the bone mineral image Ge. A pattern according to the muscle mass distribution is added to the muscle image Gm.

Note that, regarding the bone mineral image Ge, in FIG. 8, for the sake of simplicity, the pattern representing the bone mineral density is added only to the femur. Below the bone mineral image Ge, a reference 51 representing the magnitude of the bone mineral density for the added pattern is displayed. An operator can easily recognize the bone mineral density by interpreting the bone mineral image Ge while referring to the reference 51. Note that different colors may be added to the bone mineral image Ge depending on the bone mineral density instead of the pattern.

In addition, regarding the muscle image Gm, for the sake of description, an outline of the bone region is shown by a broken line in the muscle image Gm. In addition, in FIG. 8, for the sake of simplicity, a pattern representing the muscle mass is added only in the vicinity of the femur. Below the muscle image Gm, a reference 52 representing the magnitude of the muscle mass for the added pattern is displayed. The operator can easily recognize the muscle mass by interpreting the muscle image Gm while referring to the reference 52. Note that different colors may be added to the muscle image Gm depending on the muscle mass instead of the pattern.

In the following, the derivation of the body thickness, the bone mineral density, and the muscle mass included in the correct answer data 42 of the teacher data 40 will be described.

Figure 9:
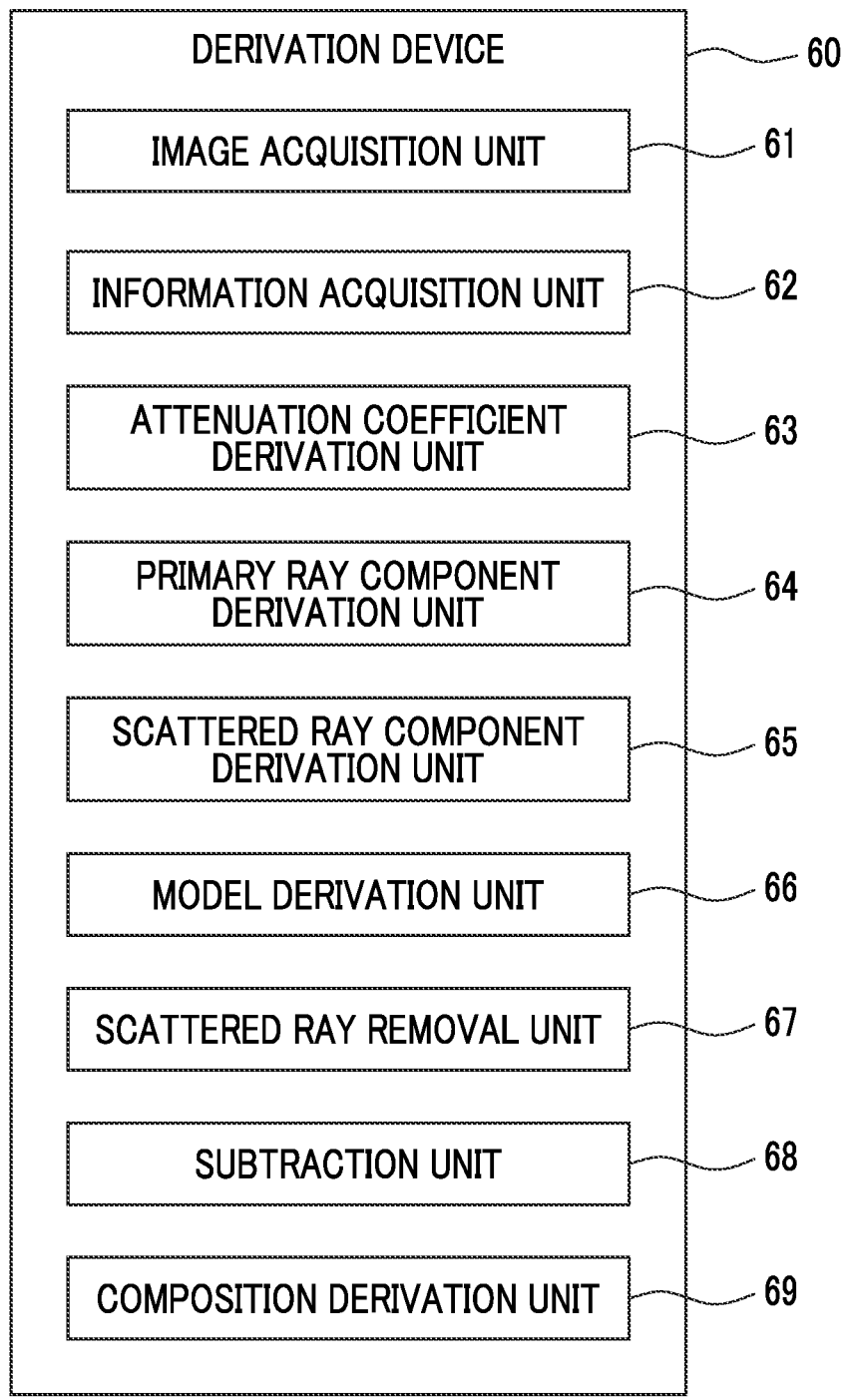
FIG. 9 is a diagram showing a functional configuration of a correct answer data derivation device.

FIG. 9 is a diagram showing a functional configuration of a derivation device that derives the body thickness, the bone mineral density, and the muscle mass included in the correct answer data 42. Note that a derivation device 60 is a computer, such as a workstation, a server computer, and a personal computer, and has the same hardware configuration as the learning device and the radiation image processing device according to the present embodiment shown in FIG. 2. In the derivation device 60, the CPU executes a derivation program to derive a scattered ray model from the standard image, and the scattered ray model is used to derive the body thickness, the bone mineral density, and the muscle mass.

As shown in FIG. 9, the derivation device 60 comprises an image acquisition unit 61, an information acquisition unit 62, an attenuation coefficient derivation unit 63, a primary ray component derivation unit 64, a scattered ray component derivation unit 65, a model derivation unit 66, a scattered ray removal unit 67, a subtraction unit 68, and a composition derivation unit 69. Moreover, the CPU of the derivation device 60 executes the derivation program, and the CPU of the derivation device 60 functions as the image acquisition unit 61, the information acquisition unit 62, the attenuation coefficient derivation unit 63, the primary ray component derivation unit 64, the scattered ray component derivation unit 65, the model derivation unit 66, the scattered ray removal unit 67, the subtraction unit 68, and the composition derivation unit 69.

In a case of deriving the scattered ray model, the image acquisition unit 61 acquires a standard image K0 by causing the imaging apparatus 1 to image a standard object simulating a human body. In this case, only one radiation detector is used. Note that, in a case in which the standard image K0 is stored in the image storage system 9, the image acquisition unit 61 acquires the standard image K0 from the image storage system 9.

Figure 10:
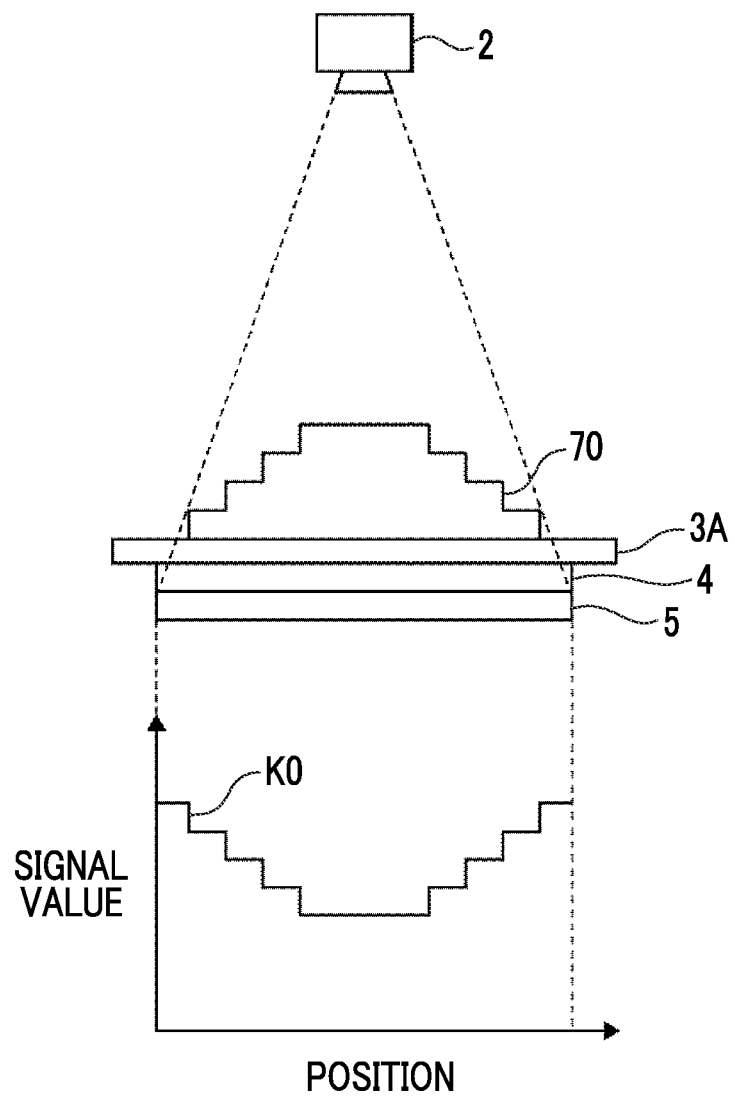
FIG. 10 is a diagram for describing imaging of a standard object.

FIG. 10 is a diagram for describing imaging of the standard object. Note that the standard object is imaged by the imaging apparatus 1 shown in FIG. 1. As shown in FIG. 10, a standard object 70 is made of a material having different thickness portions, such as 5 cm, 10 cm, and 20 cm, in stages and having the same radiation transmittance as the soft tissue (fat and muscle) of the human body. Therefore, the standard object 70 simulates a radiation characteristic of the human body. Here, the soft tissue is a mixture of the muscle and the fat in a certain ratio. A mixing ratio of the muscle and the fat differs depending on gender, physique, and the like, but can be defined by an average body fat percentage (65%). Therefore, a material, such as acrylic, which corresponds to the composition mixed at a ratio of 0.75 of the muscle and 0.65 of the fat, is used as the standard object.

In a case of acquiring the standard image K0, as shown in FIG. 10, the standard object 70 is placed on the top plate 3A of the imaging table 3, the radiation source 2 is driven to emit the radiation transmitted through the standard object 70 to the radiation detector (here, the first radiation detector 5) via the grid 4, so that the image acquisition unit 61 acquires the standard image K0. The pixel value of each pixel of the standard image K0 includes the primary ray component based on the radiation traveling straight through the standard object 70 and the scattered ray component based on the radiation scattered by the standard object 70.

Note that the standard object 70 is not limited to one object having different thicknesses as shown in FIG. 10. A plurality of standard objects having different thicknesses may be used. In this case, the standard image K0 may be acquired by imaging the plurality of standard objects at once, or the standard images corresponding to each of the standard objects may be acquired by imaging the plurality of standard objects separately.

On the other hand, in a case of deriving the composition (that is, the bone mineral density and the muscle mass) of the subject H, the image acquisition unit 61 acquires the first radiation image G1 and the second radiation image G2 of the subject H from the first and second radiation detectors 5 and 6 by causing the imaging apparatus 1 to image the subject H. Note that, in a case in which the first radiation image G1 and the second radiation image G2 are stored in the image storage system 9, the image acquisition unit 61 acquires the first radiation image G1 and the second radiation image G2 from the image storage system 9.

In a case in which the standard image K0, the first radiation image G1, and the second radiation image G2 are acquired, the imaging condition, such as the dose, the radiation quality, the SID, and the SOD at the time of imaging, and the presence or absence of the grid 4, are set.

The information acquisition unit 62 acquires the imaging condition set at the time of imaging. In addition, the information acquisition unit 62 acquires the energy characteristic of the radiation at the time of imaging the standard object 70. The energy characteristic of the radiation may be acquired from the imaging apparatus 1, or the energy characteristic of the radiation may be stored in the image storage system 9 and acquired from the image storage system 9. Note that a nominal value of the imaging apparatus 1 may be used for the energy characteristic, since there are individual differences in the characteristic of the devices, it is preferable to measure the energy characteristic in advance by using a semiconductor dosimeter.

Here, the energy characteristic is defined by any one of (i) an energy spectrum of the radiation emitted from the radiation source 2, (ii) the tube voltage [kV] and a total filtration amount [mmA1 equivalent], or (iii) the tube voltage [kV] and an aluminum half-valent layer [mmA1]. The energy spectrum of the radiation is obtained by plotting a relationship between the number of relative radiation photons with respect to the radiation energy [keV]. The tube voltage means the maximum value of the generated radiation energy distribution. The total filtration amount is obtained by converting the filtration amount of each constituting component which configures the imaging apparatus 1, such as a radiation generator and a collimator, in the radiation source 2 into a thickness of the aluminum. The influence of the beam hardening in the imaging apparatus 1 is larger and the total amount of high-energy components in the wavelength distribution of the radiation is larger as the total filtration amount is larger. The half-value layer is defined by the thickness of the aluminum necessary to attenuate the dose in half with respect to the generated radiation energy distribution. The high-energy components in the wavelength distribution of the radiation is larger as the aluminum in the half-value layer is thicker.

Figure 11:
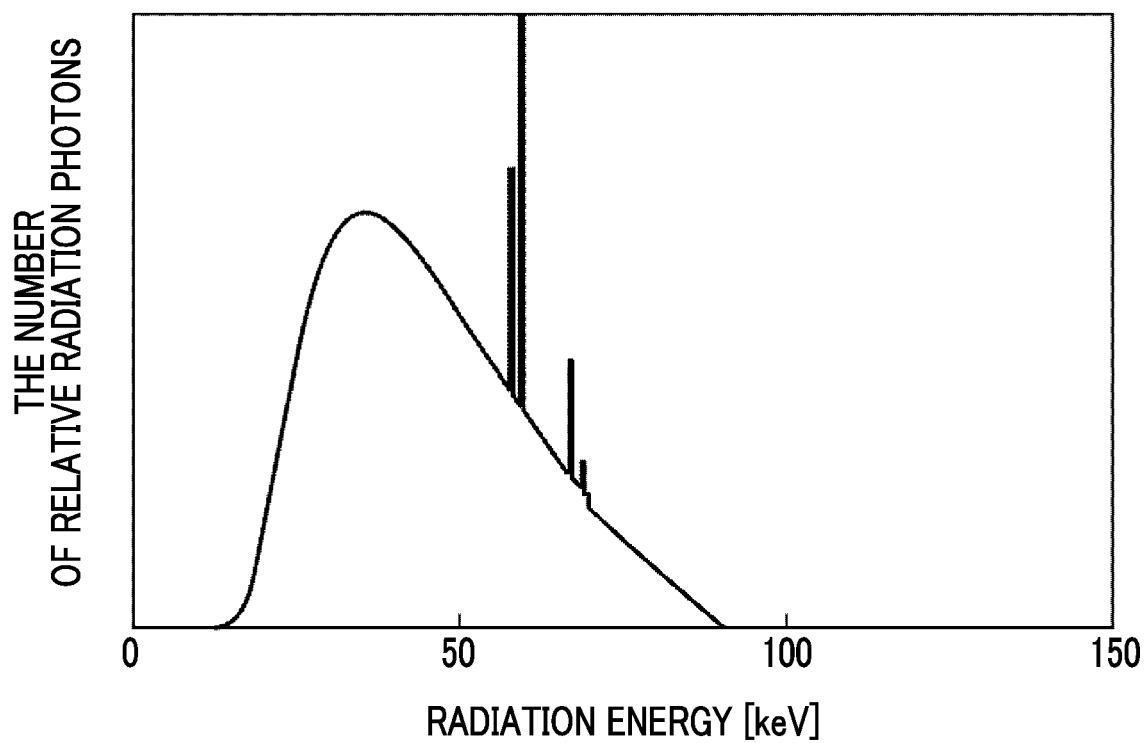
FIG. 11 is a diagram showing an energy spectrum of radiation.

FIG. 11 is a diagram showing an energy spectrum of the radiation. In FIG. 11, the energy spectrum corresponds to the tube voltage of 90 kV and the total filtration amount of 2.5 mmA1. Note that the total filtration amount of 2.5 mmA1 corresponds to the half-value layer 2.96 mmA1.

By using the energy characteristic of the radiation, the attenuation coefficient derivation unit 63 derives a relationship between the thickness of the standard object 70 and the radiation attenuation coefficient of the standard object 70, which reflects the influence of the beam hardening of the object present between the standard object 70 and the radiation detector 5.

The attenuation coefficient derivation unit 63 first derives the energy spectrum of the radiation from the energy characteristic of the radiation acquired by the information acquisition unit 62 by using a well-known Tucker approximation formula or the like. Note that the energy characteristic acquired by the information acquisition unit 62 is the energy spectrum of the radiation, the acquired energy spectrum need only be used as it is.

Moreover, the attenuation coefficient derivation unit 63 derives the radiation attenuation coefficient depending on the thickness of the standard object 70 by simulating the spectrum of the radiation by using a radiation attenuation characteristic of the soft tissue of the human body.

Figure 12:
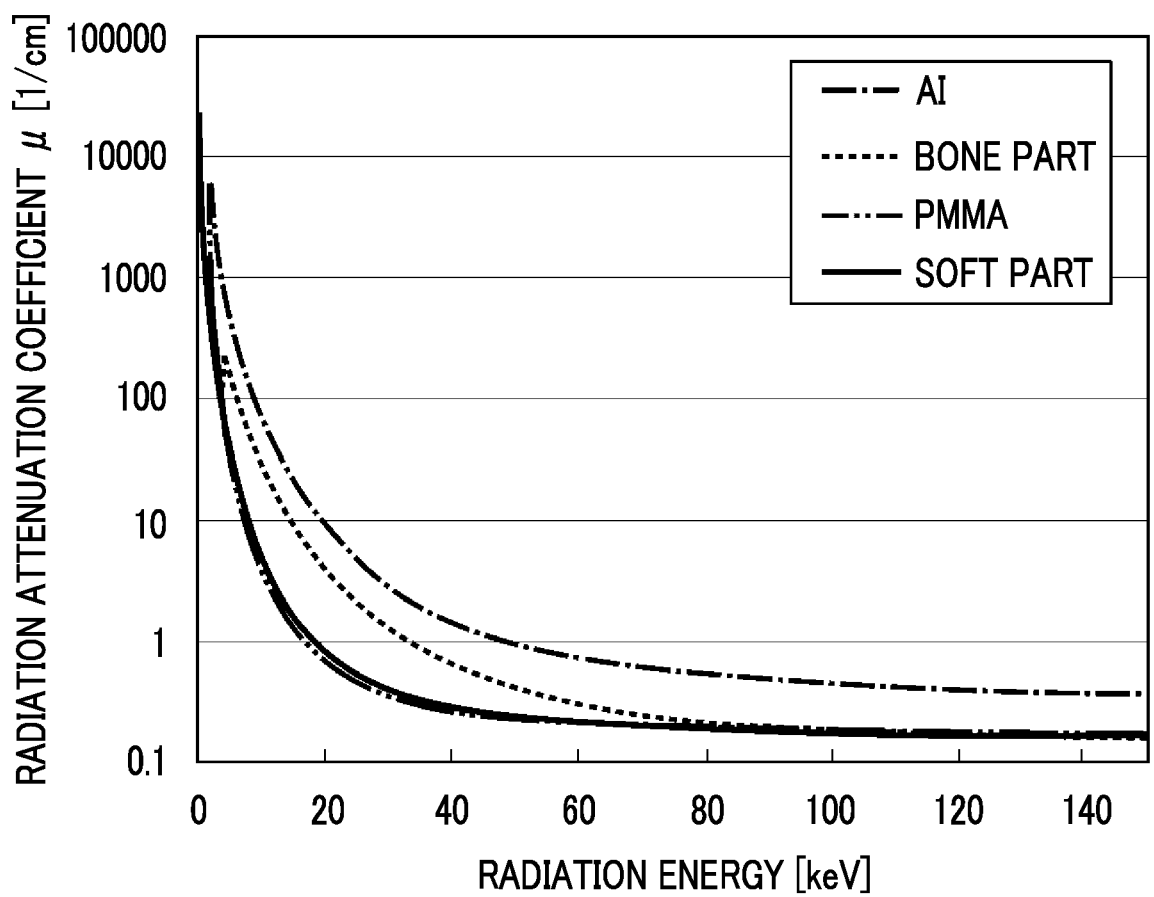
FIG. 12 is a diagram showing radiation attenuation coefficients of a soft tissue, a bone tissue, and aluminum of a human body with respect to radiation energy.

Here, in a case in which the energy spectrum of the radiation emitted from the radiation source 2 is defined as $S_{in}(E)$ and the thickness of the standard object 70 is defined as t, the radiation dose Xbody(t) after being transmitted through the standard object 70 can be calculated by Expression (1) using a radiation attenuation characteristic $\mu Soft(E)$ of the soft tissue of the human body. Note that the radiation attenuation coefficients of the soft tissue, the bone tissue, and the aluminum of the human body with respect to the radiation energy are known as shown in FIG. 12. The aluminum is the interspace material for the grid 4. Here, FIG. 12 also shows the radiation attenuation coefficient of the acrylic (polymethyl methacrylate, PMMA), which is the material of the standard object 70. The radiation attenuation coefficient of the acrylic is substantially the same as the radiation attenuation coefficient of the soft tissue of the human body, as shown in FIG. 12.

$$X_{body}(t) = \int_0^\infty S_{in}(E) \times \exp\{-\mu_{Soft}(E) \times t\} dE \quad (1)$$

On the other hand, as shown in FIG. 1, in a case in which the standard object 70 is imaged by the imaging apparatus 1, the top plate 3A and the grid 4 are present between the standard object 70 and the radiation detectors 5 and 6. A material of the top plate 3A is the acrylic and the interspace material of the grid 4 is the aluminum. In a case in which the radiation attenuation coefficient of the acrylic is defined as $\mu PMMA(E)$, the thickness of the top plate 3A (that is, the thickness of the acrylic) is defined as tPMMA, the radiation attenuation characteristic of the aluminum is defined as $\mu Al(E)$, and the thickness of grid 4 (that is, the aluminum)

is defined as tA1, an X-ray dose Xout(t) after being transmitted through the top plate 3A and the grid 4 is represented by Expression (2).

$$X_{out}(t)=\int_0^\infty S_{in}(E)\times\exp\{-\mu_{Soft}(E)\times t\}\times\exp\{-\mu_{PMMA}(E)\times t_{PMMA}\}\times\exp\{-\mu_{A1}(E)\times t_{A1}\}dE \qquad (2)$$

Note that, in a case in which the material of the top plate 3A and the interspace material of the grid 4 are unknown, the X-ray dose Xout(t) after being transmitted through the top plate 3A and the grid 4 cannot be derived by Expression (2). In this case, the energy characteristic (kV, TF0) of the radiation emitted from the radiation source 2 and the energy characteristic (kV, TF1) of the radiation after being transmitted through the top plate 3A and the grid 4 are measured using a dosimeter, and the X-ray dose Xout(t) after being transmitted through the top plate 3A and the grid 4 can be derived by Expression (2-1) using the energy characteristic (kV, TF0) and the energy characteristic (kV, TF1). Note that the energy characteristic in Expression (2-1) represents the total filtration amount (mmA1 equivalent) of the radiation emitted by a certain tube voltage [kV].

$$X_{out}(t)=\int_0^\infty S_{in}(E)\times\exp\{-\mu_{Soft}(E)\times t\}\times\exp\{-\mu_{in}(E)\times(TF1-TF0)\}dE \qquad (2\text{-}1)$$

The radiation attenuation coefficient of the standard object 70 in the imaging system including the top plate 3A and the grid 4 is obtained by representing an attenuation ratio of the radiation after being transmitted through the standard object 70 by an attenuation index as shown in Expression (3) with reference to the radiation dose in a case in which the standard object 70 is not present (that is, in a case in which the thickness of the standard object 70 is 0).

$$\frac{X_{out}(t)}{X_{out}(0)}=\exp\{-\mu_{Soft}(t)\times t\} \qquad (3)$$

By solving Expression (3) with respect to the radiation attenuation coefficient μSoft(t) of the soft tissue as shown in Expression (4), a relationship between a thickness t of the standard object 70 and the radiation attenuation coefficient can be derived.

$$\mu_{Soft}(t)=-\frac{\ln\left\{\frac{X_{out}(t)}{X_{out}(0)}\right\}}{t} \qquad (4)$$

Figure 13:
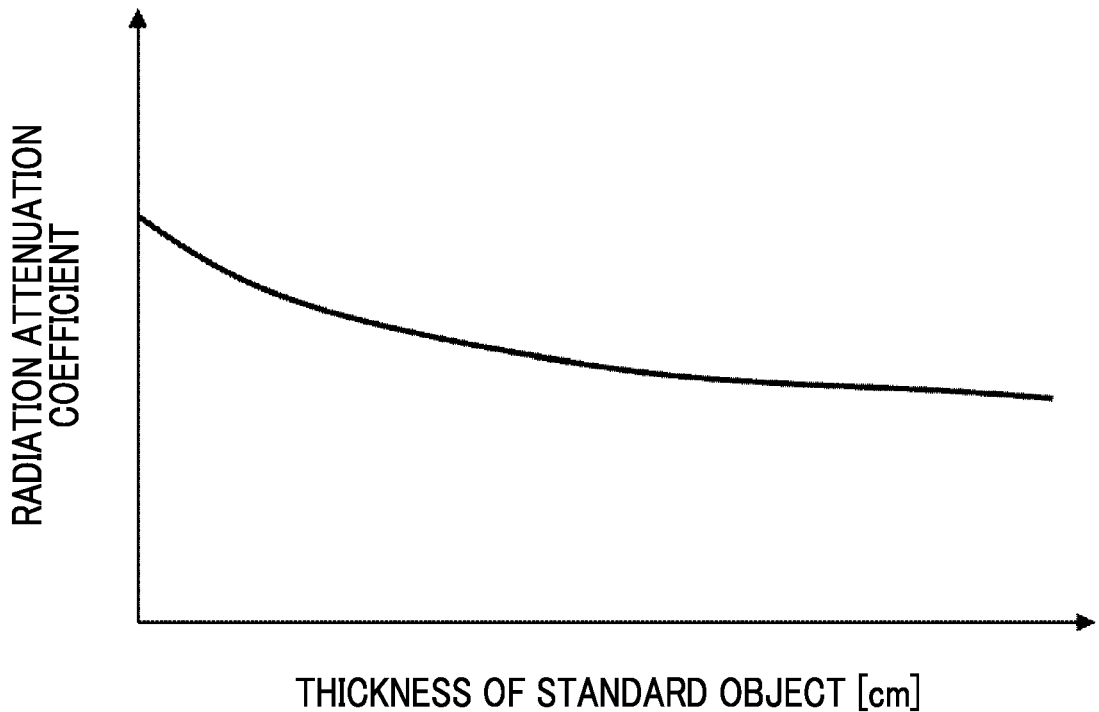
FIG. 13 is a diagram showing a relationship between a thickness of the standard object and the radiation attenuation coefficient.

The standard object 70 has a plurality of different thicknesses in stages. Therefore, the attenuation coefficient derivation unit 63 derives the radiation attenuation coefficient by Expression (4) for each of the plurality of thicknesses of the standard object 70. Moreover, the attenuation coefficient derivation unit 63 derives the relationship between the thickness t of the standard object 70 and the radiation attenuation coefficient by performing an interpolation calculation using the radiation attenuation coefficient of the thickness present in the standard object 70 for the radiation attenuation coefficient of the thickness that is not present in the standard object 70. FIG. 13 is a diagram showing a relationship between the thickness t of the standard object 70 and the radiation attenuation coefficient. FIG. 13 shows the relationship between the thickness of the standard object 70 and the radiation attenuation coefficient in a case in which the tube voltage is 90 kV and the total filtration amount is 2.5 mmA1. The attenuation coefficient derivation unit 63 derives the relationship between the thickness of the standard object 70 and the radiation attenuation coefficient for each energy characteristic of the radiation, and stores the derived relationship in the storage of the derivation device 60.

The primary ray component derivation unit 64 derives the radiation attenuation coefficient corresponding to the thickness of the standard object 70 based on the relationship between the thickness of the standard object 70 and the radiation attenuation coefficient derived by the attenuation coefficient derivation unit 63. Moreover, the primary ray component included in the standard image K0 is derived based on the radiation attenuation coefficient corresponding to the thickness of the standard object 70.

Here, in a case in which the pixel value of each pixel of the standard image K0 is defined as I0o(x,y), the thickness of the standard object 70 corresponding to each pixel of the standard image K0 is defined as T0(x,y), and the radiation attenuation coefficient derived by Expression (4) with respect to the thickness T0(x,y) of each pixel of the standard image K0 is defined as μSoft0(x,y), the primary ray component derivation unit 64 derives a primary ray component I0p(x,y) included in the pixel value of each pixel of the standard image K0 by Expression (5). Note that since the standard object 70 has the plurality of thicknesses in stages, the primary ray component derivation unit 64 derives the primary ray component I0p(x,y) for each thickness present in the standard object 70. Note that the primary ray component derivation unit 64 may derive the relationship between the thickness of the standard object 70 and the primary ray component by performing the interpolation calculation using the primary ray component of the thickness that is present in the standard object 70 for the primary ray component corresponding to the thickness that is not present in the standard object 70.

$$I0p(x,y)=I0o(x,y)\times\exp(-\mu Soft0(x,y)\times T0(x,y)) \qquad (5)$$

The scattered ray component derivation unit 65 derives the scattered ray component included in the standard object 70 based on the difference between the pixel value of the standard image K0 and the primary ray component. That is, the scattered ray component derivation unit 65 derives a scattered ray component I0s(x,y) by Expression (6). Note that since the standard object 70 has the plurality of thicknesses in stages, the scattered ray component I0s(x,y) corresponding to the stepwise thickness of the standard object 70 is derived. Note that the scattered ray component derivation unit 65 may derive the relationship between the thickness of the standard object 70 and the scattered ray component by performing the interpolation calculation using the scattered ray component of the thickness that is present in the standard object 70 for the scattered ray component corresponding to the thickness that is not present in the standard object 70.

$$I0s(x,y)=I0o(x,y)-I0p(x,y) \qquad (6)$$

The model derivation unit 66 derives the scattered ray model representing the relationship between the thickness of the standard object 70 and the ratio of the scattered ray component I0s(x,y) to the primary ray component I0p(x,y). That is, the model derivation unit 66 derives the scattered ray model by calculating the ratio (that is, I0s(x,y)/I0p(x,y)) of the scattered ray component I0s(x,y) to the primary ray component I0p(x,y) as a scatter-to-primary ratio (STPR) for each thickness of the standard object 70 and plotting a relationship between the thickness of the standard object 70 and the STPR. Note that since the thicknesses of the standard object 70 are different in stages, the STPR at the thickness that is not present at the standard object 70 need only be derived by the interpolation calculation using the STPR at the thickness that is present in the standard object 70.

Figure 14:
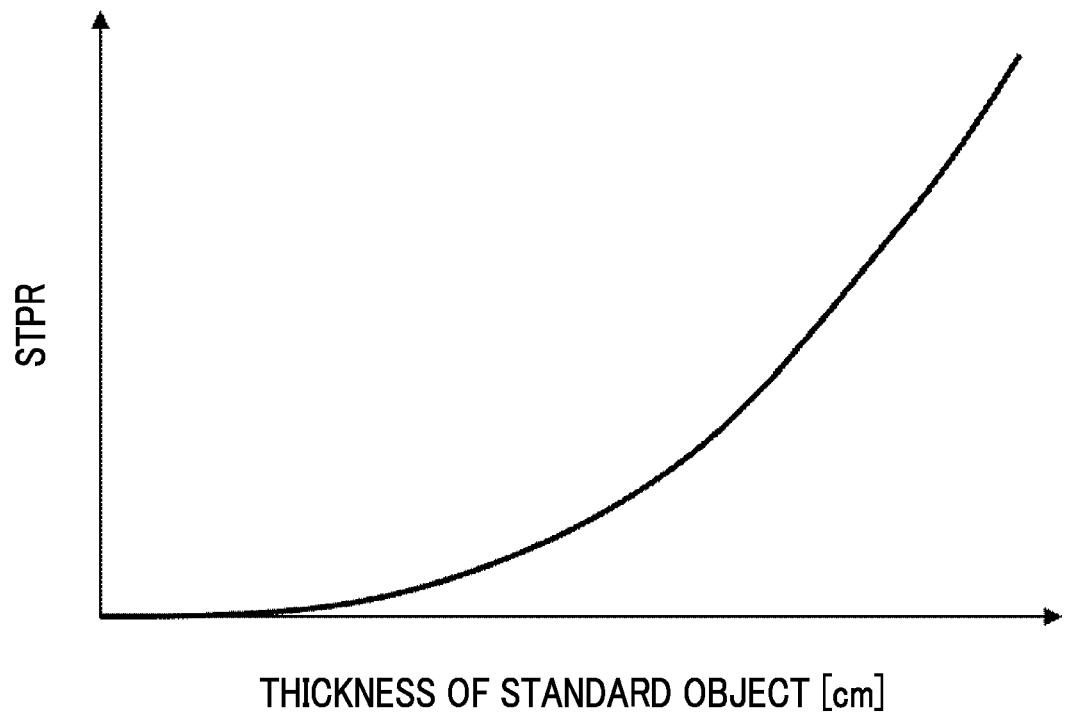
FIG. 14 shows a scattered ray model.

FIG. 14 is a diagram showing the scattered ray model. FIG. 14 shows a relationship between the thickness of the standard object 70 and the STPR in a case in which the tube voltage is 90 kV and the total filtration amount is 2.5 mmA1. The model derivation unit 66 stores the derived scattered ray model in the storage of the derivation device 60. Note that the standard object 70 simulates the radiation characteristic of the human body. Therefore, the scattered ray model shown in FIG. 14 represents the relationship between the thickness of the subject H and the STPR.

Note that the scattered ray model need only be derived for each energy characteristic of the radiation that can be emitted by the radiation source 2 of the imaging apparatus 1 and stored in the storage of the derivation device 60.

The scattered ray removal unit 67 removes the scattered ray component from each of the first radiation image G1 and the second radiation image G2 acquired by the image acquisition unit 61 by using the scattered ray model derived by the model derivation unit 66. In the following, the removal of the scattered ray component will be described. As a method for removing the scattered ray component, for example, any method, such as a method disclosed in JP2015-043959A, can be used. In the following, scattered ray removal processing in a case in which the method disclosed in JP2015-043959A is used will be described. Note that, in the following description, G1 and G2 will be used as reference numerals for the first and second radiation images from which the scattered ray component is removed.

First, the scattered ray removal unit 67 acquires a virtual model of the subject H having an initial body thickness distribution Ts(x,y). The virtual model is data virtually representing the subject H of which a body thickness in accordance with the initial body thickness distribution Ts(x, y) is associated with a coordinate position of each pixel of the first radiation image G1. Note that the virtual model of the subject H having the initial body thickness distribution Ts(x,y) is stored in the storage of the derivation device 60 in advance, but the virtual model may be acquired from an external server in which the virtual model is stored.

Next, as shown in Expression (7) and Expression (8), the scattered ray removal unit 67 derives an estimated primary ray image Ip(x,y) obtained by estimating a primary ray image obtained by imaging the virtual model and an estimated scattered ray image Is(x,y) obtained by estimating a scattered ray image obtained by imaging the virtual model, based on the virtual model. Moreover, as shown in Expression (9), the scattered ray removal unit 67 derives an image obtained by combining the estimated primary ray image Ip(x,y) and the estimated scattered ray image Is(x,y) as an estimated image Im(x,y) obtained by estimating the first radiation image G1 obtained by imaging the subject H.

$$Ip(x,y)=Io(x,y)\times\exp(-\mu \text{Soft}(x,y)\times T(x,y)) \quad (7)$$

$$Is(x,y)=Io(x,y)\times \text{STPR}(T(x,y))*PSF(T(x,y)) \quad (8)$$

$$Im(x,y)=Is(x,y)+Ip(x,y) \quad (9)$$

Here, (x,y) is a coordinate of a pixel position of the first radiation image G1, Io(x,y) is a pixel value of the first radiation image G1 at the pixel position (x,y), Ip(x,y) is the primary ray component at the pixel position (x,y), and Is(x,y) is the scattered ray component at the pixel position (x,y). Note that, in a case of deriving the first estimated image Im(x,y), the initial body thickness distribution Ts(x,y) is used as the body thickness distribution T(x,y) in Expression (7) and Expression (8). In addition, μSoft (T(x,y)) in Expression (7) is derived by referring to the relationship between the thickness t of the standard object 70 shown in FIG. 13 and the radiation attenuation coefficient derived by the attenuation coefficient derivation unit 63. In addition, the STPR (T(x,y)) in Expression (8) is derived by referring to the scattered ray model shown in FIG. 14 derived by the model derivation unit 66 based on the energy characteristic of the radiation used at the time of imaging the subject H.

In addition, the PSF (T(x,y)) in Expression (8) is a point spread function representing the distribution of the scattered rays spreading from one pixel depending on the body thickness distribution T(x,y), and is defined depending on the energy characteristic of the radiation. In addition, * is an operator representing a convolution operation. The PSF is also changed due to a distribution of irradiation fields in the imaging apparatus 1, a distribution of the compositions of the subject H, the irradiation dose at the time of imaging, the tube voltage, an imaging distance, the characteristics of the radiation detectors 5 and 6, and the like. Therefore, the PSF need only be experimentally obtained in advance for each energy characteristic of the radiation used by the imaging apparatus 1 in accordance with irradiation field information, subject information, the imaging condition, and the like, and stored in the storage of the derivation device 60.

Next, the scattered ray removal unit 67 corrects the initial body thickness distribution Ts(x,y) of the virtual model such that a difference between the estimated image Im and the first radiation image G1 is small. The scattered ray removal unit 67 updates the body thickness distribution T(x,y), the scattered ray component Is(x,y), and the primary ray component Ip(x,y) by repeating the derivation of the body thickness distribution T(x,y), the scattered ray component Is(x,y), and the primary ray component Ip(x,y) until a difference between the estimated image Im and the first radiation image G1 satisfies a predetermined termination condition. The scattered ray removal unit 67 subtracts the scattered ray component Is(x,y) derived by Expression (8) from the first radiation image G1 in a case in which the termination condition is satisfied. As a result, the scattered ray component included in the first radiation image G1 is removed. Note that the body thickness distribution T(x,y) in a case in which the termination condition is satisfied is used as the body thickness 42A of the correct answer data 42 included in the teacher data 40.

On the other hand, the scattered ray removal unit 67 also performs the scattered ray removal processing on the second radiation image G2 in the same manner as in the first radiation image G1.

The subtraction unit 68 performs energy subtraction processing to derive a bone part image Gb in which a bone part of the subject H is extracted and a soft part image Gs in which a soft part is extracted from the first and second radiation images G1 and G2, which are subjected to the scattered ray removal processing. Note that the first and second radiation images G1 and G2 in the subsequent processing are processed radiation images from which the scattered ray component is removed.

Figure 15:
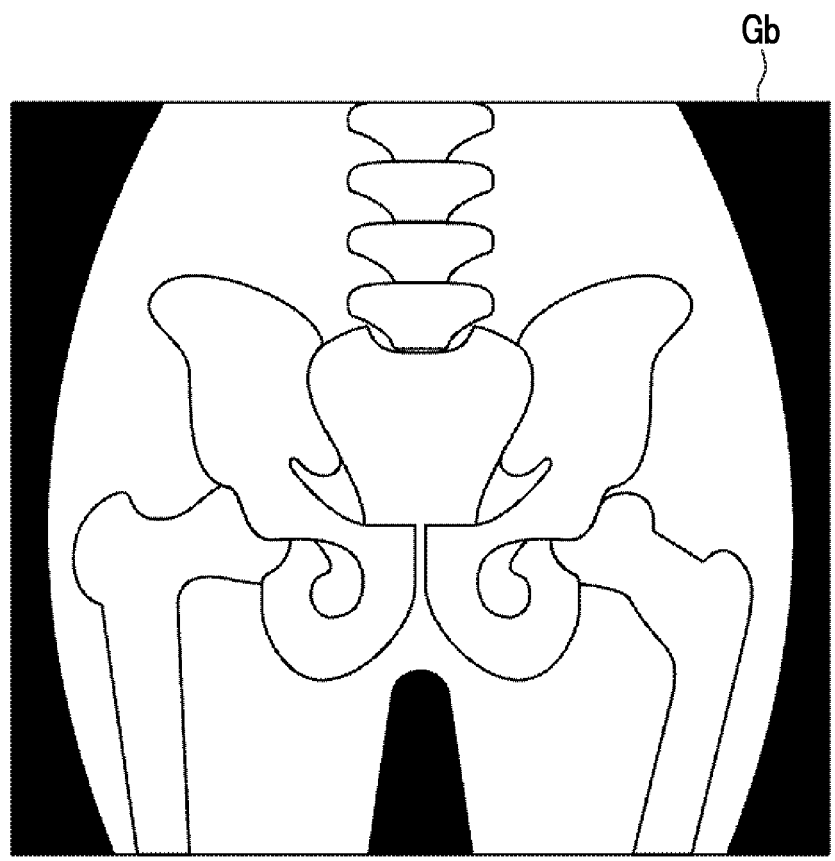
FIG. 15 is a diagram showing a bone part image.

In a case in which the bone part image Gb is derived, the subtraction unit 68 performs weighting subtraction between the corresponding pixels with respect to the first and second radiation images G1 and G2 as shown in Expression (10) to generate the bone part image Gb in which the bone part of the subject H included in each of the radiation images G1 and G2 is extracted, as shown in FIG. 15. In Expression (10), β1 is a weighting coefficient, and is set as a value capable of extracting the bone part of the subject H included in each of the radiation images G1 and G2 by Expression (10) based on the radiation attenuation coefficients of the bone tissue and the soft tissue. Note that a pixel value of each pixel in a bone region in the bone part image Gb is a bone part pixel value.

$$Gb(x,y)=G1(x,y)-\beta1\times G2(x,y) \quad (10)$$

Figure 16:
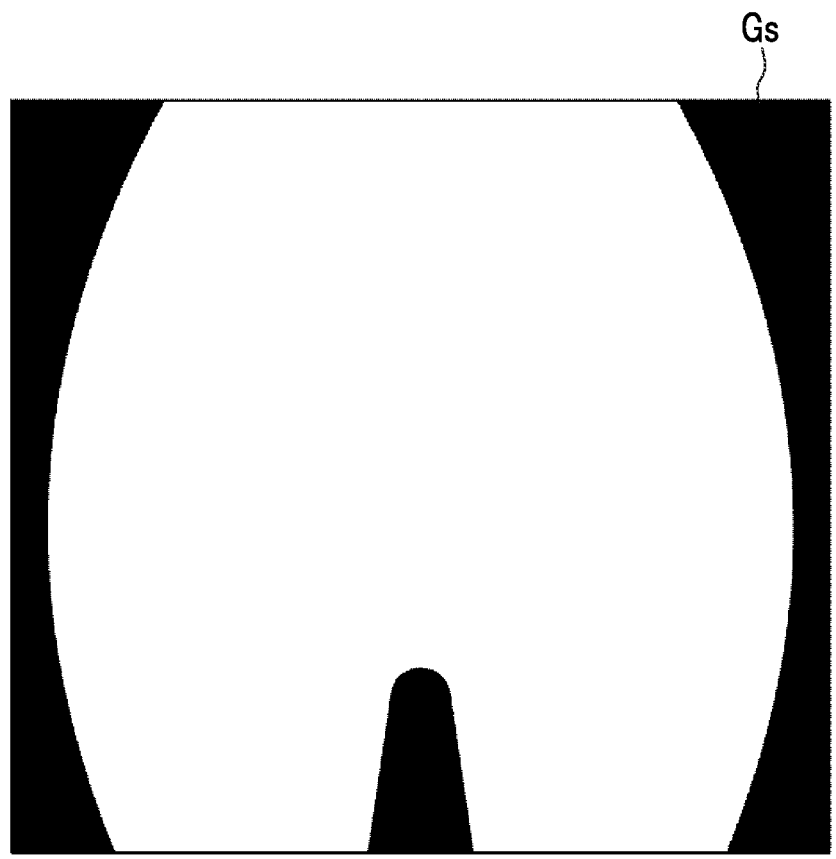
FIG. 16 is a diagram showing a soft part image.

On the other hand, in a case in which the soft part image Gs is derived, the subtraction unit 68 performs weighting subtraction between the corresponding pixels with respect to the first and second radiation images G1 and G2 as shown in Expression (11) to generate the soft part image Gs in which the soft part of the subject H included in each of the radiation images G1 and G2 is extracted, as shown in FIG. 16. In Expression (11), β2 is a weighting coefficient, and is set as a value capable of extracting the soft part of the subject H included in each of the radiation images G1 and G2 by Expression (11) based on the radiation attenuation coefficients of the bone tissue and the soft tissue.

$$Gs(x,y)=G1(x,y)-\beta2\times G2(x,y) \quad (11)$$

Note that the soft part image Gs shows a soft region due to a soft tissue of the subject H. In the present embodiment, the "soft tissue" of the subject H refers to a tissue other than a bone tissue, and specifically includes a muscle tissue, a fat tissue, blood, and water.

The composition derivation unit 69 derives the composition of the subject H. Specifically, the composition derivation unit 69 derives the bone mineral density as the composition for each pixel of the bone region of the bone part image Gb based on the pixel value of the bone part image Gb. In addition, the composition derivation unit 69 derives the muscle mass as the composition for each pixel of the soft region in the soft part image Gs. First, the derivation of the bone mineral density will be described.

The composition derivation unit 69 derives the bone mineral density for each pixel of the bone part image Gb. In the present embodiment, the composition derivation unit 69 derives a bone mineral density by converting each pixel value of the bone part image Gb into the pixel value of the bone part image acquired under a standard imaging condition. Specifically, the composition derivation unit 69 derives the bone mineral density by correcting each pixel value of the bone part image Gb by using a correction coefficient acquired from a look-up table described below.

Here, the contrast between the soft part and the bone part in the radiation image is lower as the tube voltage in the radiation source 2 is higher and the energy of the radiation emitted from the radiation source 2 is higher. In addition, in a procedure of the radiation transmitted through the subject H, a low-energy component of the radiation is absorbed by the subject H, and beam hardening occurs in which the radiation energy is increased. The increase in the radiation energy due to the beam hardening is larger as the body thickness of the subject H is larger.

Figure 17:
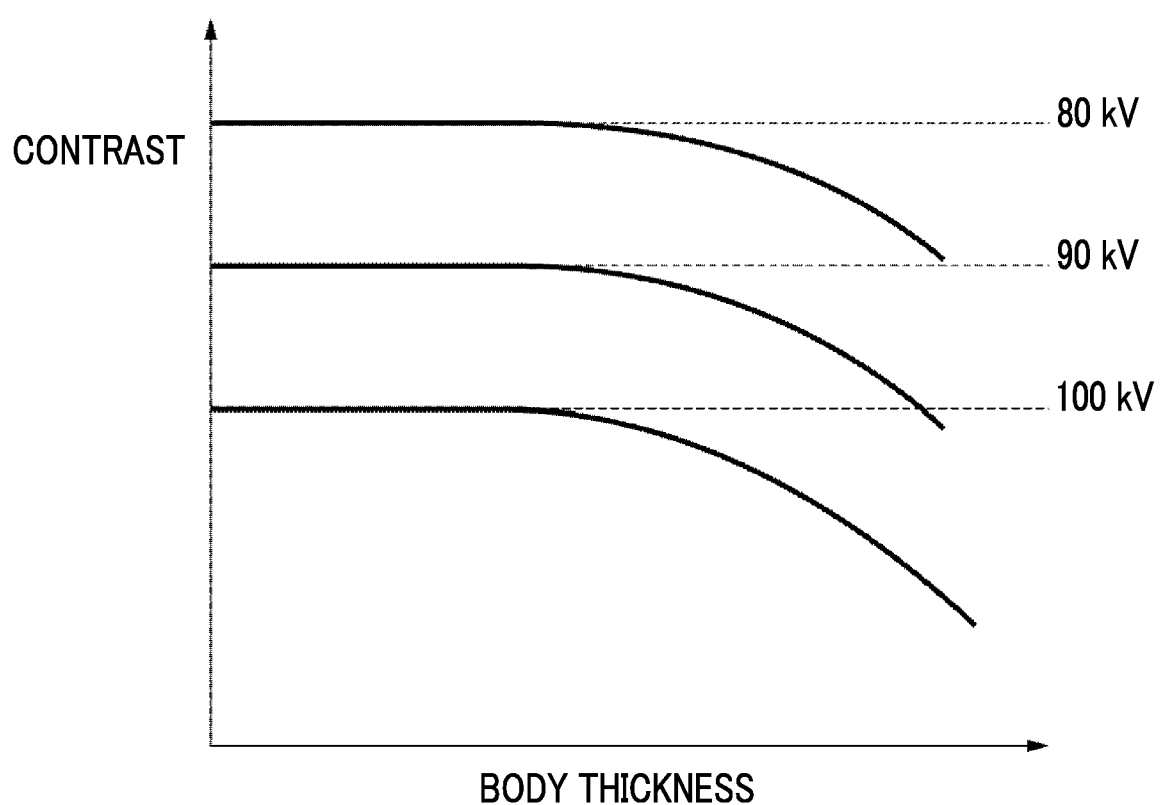
FIG. 17 is a diagram showing a relationship of a contrast between a bone part and a soft part with respect to a body thickness of a subject.

FIG. 17 is a diagram showing a relationship of the contrast between the bone part and the soft part with respect to the body thickness of the subject H. Note that FIG. 17 shows the relationship of the contrast between the bone part and the soft part with respect to the body thickness of the subject H at the three tube voltages of 80 kV, 90 kV, and 100 kV. As shown in FIG. 17, the contrast is lower as the tube voltage is higher. In addition, in a case in which the body thickness of the subject H exceeds a certain value, the contrast is lower as the body thickness is larger. Note that contrast between the bone part and the soft part is higher as the pixel value of the bone region in the bone part image Gb is larger. Therefore, the relationship shown in FIG. 17 shifts to a higher contrast side as the pixel value of the bone region in the bone part image Gb is increased.

In the present embodiment, the look-up table for acquiring the correction coefficient for correcting the difference in the contrast depending on the tube voltage at the time of imaging and the reduction in the contrast due to the influence of the beam hardening in the bone part image Gb is stored in the storage of the derivation device 60. The correction coefficient is the coefficient for correcting each pixel value of the bone part image Gb.

Figure 18:
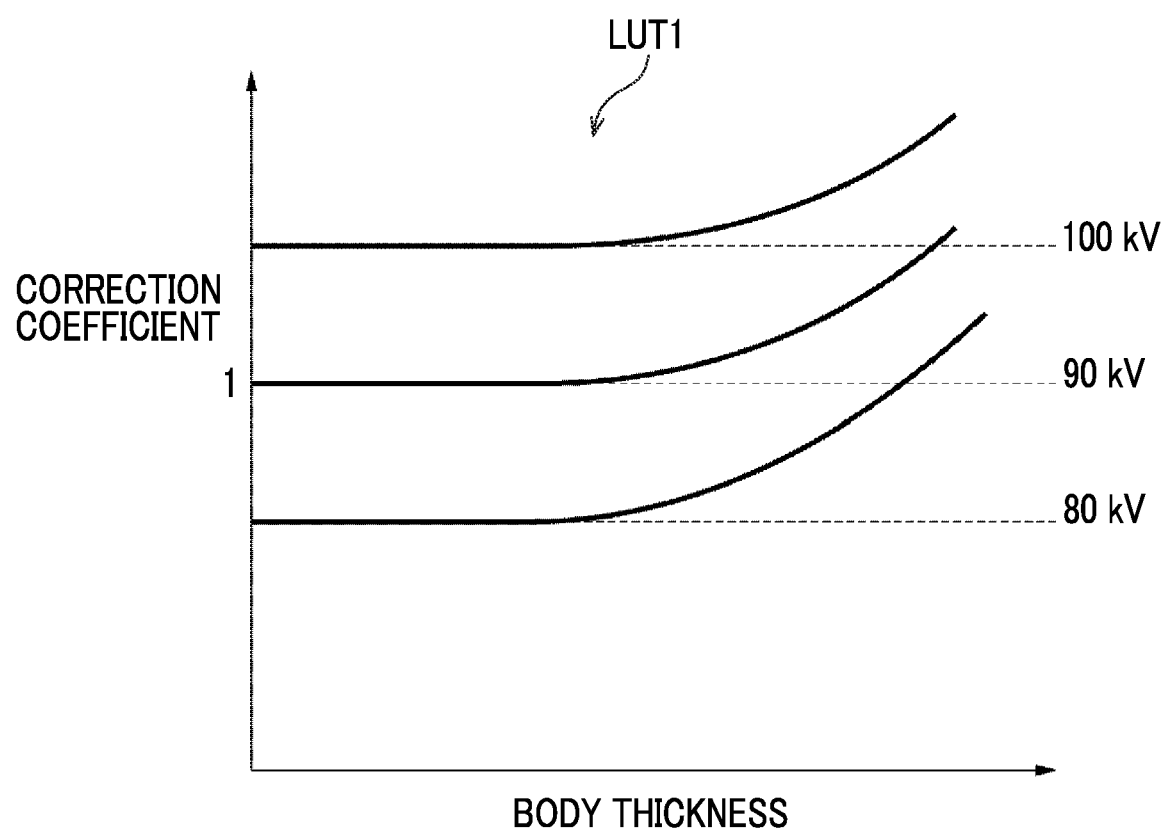
FIG. 18 is a diagram showing an example of a look-up table.

FIG. 18 is a diagram showing an example of the look-up table stored in the storage of the derivation device 60. In FIG. 18, a look-up table LUT1 in which the standard imaging condition is set to the tube voltage of 90 kV is shown. As shown in FIG. 18, in the look-up table LUT1, the correction coefficient is set to be larger as the tube voltage is higher and the body thickness of the subject H is larger. In the example shown in FIG. 18, since the standard imaging condition is the tube voltage of 90 kV, the correction coefficient is 1 in a case in which the tube voltage is 90 kV and the body thickness is 0. Note that although the look-up table LUT1 is shown in two dimensions in FIG. 18, the correction coefficient differs depending on the pixel value of the bone region. Therefore, the look-up table LUT1 is actually a three-dimensional table to which an axis representing the pixel value of the bone region is added.

The composition derivation unit 69 extracts the body thickness distribution T(x,y) of the subject H and a correction coefficient C0(x,y) for each pixel depending on a set value of the tube voltage of the radiation source 2 included in the imaging condition stored in the storage of the derivation device 60 from the look-up table LUT1. As the body thickness distribution T(x,y) of the subject H, the body thickness distribution T(x,y) in a case in which the termination condition is satisfied in the scattered ray removal unit 67 is used. Moreover, as shown in Expression (12), the composition derivation unit 69 multiplies the pixel value Gb(x,y) of each pixel of the bone region in the bone part image Gb by the correction coefficient C0(x,y) to derive the bone mineral density B(x,y) (g/cm²) for each pixel of the bone part image Gb. The bone mineral density B(x,y) derived in this way is acquired by imaging the subject H by the tube voltage of 90 kV, which is the standard imaging condition, and shows the pixel value of the bone region included in the radiation image from which the influence of the beam hardening is removed. The bone mineral density B(x,y) derived by Expression (12) is used as the bone mineral density 42B of the correct answer data 42 included in the teacher data 40.

$$B(x,y)=C0(x,y)\times Gb(x,y) \quad (12)$$

Here, it is possible to derive the correction coefficient C0(x,y) as follows. First, the radiation attenuation coefficient of the bone tissue depending on the thickness of the soft tissue of the subject H is derived. A state is assumed in which the soft tissue and the bone tissue overlap on a radiation transmission path, and in a case in which the thickness of the soft tissue is defined as tsoft, the radiation attenuation coefficient can be derived as a function depending on the thickness of the soft tissue. In a case in which the energy spectrum of the radiation emitted from the radiation source 2 is defined as Sin(E) and the thickness of the soft tissue of the subject H is defined as tsoft, a radiation dose Xout1 (tsoft) after being transmitted through the subject H in a case in which the bone tissue is not present can be calculated by Expression (13) for each thickness t of the subject H using the radiation attenuation characteristic μSoft(E) of the soft tissue of the human body. Note that, in Expression (13), as in Expression (2), the radiation attenuation coefficient of the object (that is, the top plate 3A and the grid 4) that is present between the subject H and the radiation detectors 5 and 6 is taken into consideration.

$$X_{out1}(t)=\int_0^\infty S_{in}(E)\times\exp\{-\mu_{Soft}(E)\times t_{Soft}\}\times\exp\{-\mu_{PMMA}(E)\times t_{PMMA}\}\times\exp\{-\mu_{A1}(E)\times t_{A1}\}dE \quad (13)$$

A radiation dose Xout2(t) in a case in which the bone tissue is present is derived by Expression (14) further using a radiation attenuation coefficient μBone(E) of the bone tissue.

$$X_{out2}(t)=\int_0^\infty S_{in}(E)\times\exp\{-\mu_{Soft}-\mu_{Bone}(E)\times t_{Bone}\}\times\exp\{-\mu_{PMMA}(E)\times t_{PMMA}\}\times\exp\{-\mu_{A1}(E)\times t_{A1}\}dE \quad (14)$$

The radiation attenuation coefficient of the bone tissue is obtained by representing an attenuation ratio of the radiation dose due to the bone tissue by the attenuation index with reference to the radiation dose in a case in which the bone tissue is not present, as shown in Expression (15).

$$\frac{X_{out2}(t)}{X_{out1}(t)}=\exp\{-\mu_{Bone}(t)\times t_{Bone}\} \quad (15)$$

By solving Expression (15) for μBone(t) as shown in Expression (16), the relationship between the thickness t of the subject H and the radiation attenuation coefficient of the bone tissue can be derived. Note that tBone is the thickness of the bone tissue.

$$\mu_{Bone}(t)=-\frac{\ln\left\{\frac{X_{out2}(t)}{X_{out1}(t)}\right\}}{t_{Bone}} \quad (16)$$

A correction coefficient C0(t) is derived by Expression (17) in which each thickness of the subject H is multiplied by the reciprocal the attenuation coefficient of the bone region with reference to a bone contrast of the attenuation coefficient μBone (tbase) of the bone region at an average thickness tbase of the subject H defined depending on an imaging part.

$$C0(t)=\frac{\mu_{Bone}(t_{base})}{\mu_{Bone}(t)} \quad (17)$$

Then, the derivation of the muscle mass will be described. As described above, the soft tissue includes the muscle tissue, the fat tissue, the blood, and the water. In the present embodiment, a tissue other than the fat tissue in the soft tissue is regarded as the muscle tissue. That is, in the present embodiment, a non-fat tissue including the blood and the water is included in the muscle tissue to be handled as the muscle tissue.

Figure 19:
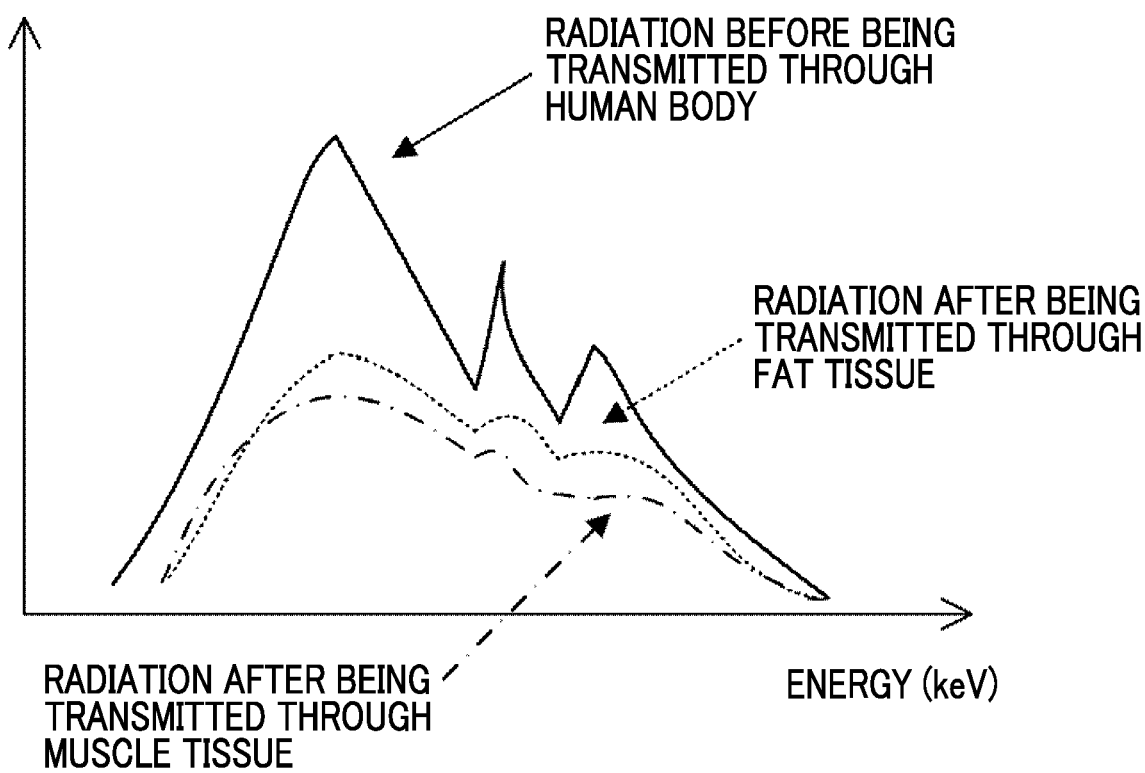
FIG. 19 is a diagram showing an example of energy spectra of the radiation after being transmitted through a muscle tissue and radiation after being transmitted through a fat tissue.

The composition derivation unit 69 separates the muscle and the fat in the soft part image Gs by using a difference in an energy characteristic between the muscle tissue and the fat tissue. Here, as shown in FIG. 19, the dose of the radiation after being transmitted through the subject H is lower than the dose of the radiation before being incident on the subject H, which is a human body. In addition, since the energy absorbed by the muscle tissue and the energy absorbed by the fat tissue is different and radiation attenuation coefficients are different, the energy spectra of the radiation after being transmitted through the muscle tissue and the radiation after being transmitted through the fat tissue in the radiation after being transmitted through the subject H are different. As shown in FIG. 19, the energy spectrum of the radiation transmitted through the subject H and emitted to each of the first radiation detector 5 and the second radiation detector 6 depends on a body composition of the subject H, specifically, a ratio between the muscle tissue and the fat tissue. Since the fat tissue is more likely to transmit the radiation than the muscle tissue, the dose of the radiation after being transmitted through the human body is smaller in a case in which the ratio of the muscle tissue is larger than the ratio of the fat tissue.

Therefore, the composition derivation unit 69 separates the muscle and the fat in the soft part image Gs by using the difference in the energy characteristic between the muscle tissue and the fat tissue described above. That is, the composition derivation unit 69 generates a muscle image and a fat image from the soft part image Gs. In addition, the composition derivation unit 69 derives the muscle mass of each pixel based on the pixel value of the muscle image.

Note that a specific method by which the composition derivation unit 69 separates the muscle and the fat from the soft part image Gs is not limited, but as an example, the composition derivation unit 69 generates the muscle image from the soft part image Gs by Expression (18) and Expression (19). Specifically, first, the composition derivation unit 69 derives a muscle ratio rm(x,y) at each pixel position (x,y) in the soft part image Gs by Expression (18). Note that, in Expression (18), μm is a weighting coefficient depending on the radiation attenuation coefficient of the muscle tissue, and μA is a weighting coefficient depending on the radiation attenuation coefficient of the fat tissue. In addition, Δ(x,y) indicates a concentration difference distribution. The concentration difference distribution is a distribution of a concentration change on the image, which is seen from a concentration obtained by making the radiation reach the first radiation detector 5 and the second radiation detector 6 without transmitted through the subject H. The distribution of the concentration change on the image is calculated by subtracting the concentration of each pixel in the region of the subject H from the concentration in a blank region obtained by directly emitting the radiation to the first radiation detector 5 and the second radiation detector 6 in the soft part image Gs.

$$rm(x,y)=\{\mu A-\Delta(x,y)/T(x,y)\}/(\mu A-\mu m) \quad (18)$$

Moreover, the composition derivation unit 69 generates a muscle image Gm from the soft part image Gs by Expression (19).

$$Gm(x,y)=rm(x,y)\times Gs(x,y) \quad (19)$$

Moreover, as shown in Expression (20), the composition derivation unit 69 derives the muscle mass M(x,y) (g/cm$^2$) for each pixel of the muscle image Gm by multiplying each pixel (x,y) of the muscle image Gm by the correction coefficient C1(x,y) representing a relationship between a predetermined pixel value and the muscle mass. The muscle mass M(x,y) derived by Expression (20) is used as the muscle mass 42C of the correct answer data 42 included in the teacher data 40.

$$M(x,y)=C1(x,y)\times Gm(x,y) \quad (20)$$

Here, it is possible to derive the correction coefficient C1(x,y) as follows. First, the bone attenuation coefficient depending on the thickness of the soft part of the subject H is derived. A state is assumed in which the fat and the muscle overlap on a radiation transmission path, and in a case in which the thickness of the fat is defined as tA, the radiation attenuation coefficient can be derived as a function depending on the thickness of the fat.

In a case in which the energy spectrum of the radiation emitted from the radiation source 2 is defined as Sin(E) and the thickness of the fat of the subject H is defined as tA, a radiation dose Xout3(t) after being transmitted through the subject H in a case in which the muscle is not present can be calculated by Expression (21) for each thickness t of the subject H using the radiation attenuation characteristic µA(E) of the fat of the human body. Note that, in Expression (21), as in Expression (2), the radiation attenuation coefficient of the object (that is, the top plate 3A and the grid 4) that is present between the subject H and the radiation detectors 5 and 6 is taken into consideration.

$$X_{out3}(t) = \int_0^\infty S_{in}(E) \times \exp\{-\mu_A(E) \times t_A\} \times \exp\{-\mu_{PMMA}(E) \times t_{PMMA}\} \times \exp\{-\mu_{A1}(E) \times t_{A1}\} dE \quad (21)$$

A radiation dose Xout4(t) in a case in which the muscle is present is derived by Expression (22) further using a radiation attenuation coefficient µM(E) of the muscle.

$$X_{out4} = \int_0^\infty S_{in}(E) \times \exp\{-\mu_A(E) \times t_A - \mu_M(E) \times t_M\} \times \exp\{-\mu_{PMMA}(E) \times t_{PMMA}\} \times \exp\{-\mu_{A1}(E) \times t_{A1}\} dE \quad (22)$$

The radiation attenuation coefficient of the muscle is obtained by representing an attenuation ratio of the radiation dose due to the muscle by the attenuation index with reference to the radiation dose in a case in which the muscle is not present, as shown in Expression 23).

$$\frac{X_{out4}(t)}{X_{out3}(t)} = \exp\{-\mu_M(t) \times t_M\} \quad (23)$$

By solving Expression (23) for µM(t) as shown in Expression (24), the relationship between the thickness tA of the fat and the radiation attenuation coefficient of the muscle can be derived. Note that tM is the thickness of the muscle.

$$\mu_M(t) = -\frac{\ln\left(\frac{X_{out4}(t)}{X_{out3}(t)}\right)}{t_M} \quad (24)$$

A correction coefficient C1(t) is derived by Expression (25) in which each thickness of the subject H is multiplied by the reciprocal the radiation attenuation coefficient of the muscle with reference to a muscle contrast of the radiation attenuation coefficient µM (tbase) of the muscle at an average thickness tbase of the subject H defined depending on an imaging part.

$$C1(t) = \frac{\mu_M(t_{base})}{\mu_M(t)} \quad (25)$$

Then, processing performed in the present embodiment will be described. FIG. 20 is a flowchart showing learning processing performed in the present embodiment. First, the information acquisition unit 22 acquires the teacher data 40 from the image storage system 9 (step ST1), and the learning unit 23 inputs the learning data 41 included in the teacher data 40 to the neural network 30 to output the body thickness, the bone mineral density, and the muscle mass and trains the neural network 30 using the loss L0 based on the difference from the correct answer data 42 (step ST2), and the processing returns to step ST1. Moreover, the learning unit 23 repeats the processing of steps ST1 and ST2 until the termination condition is satisfied, and terminates the learning processing. As a result, the learning unit 23 constructs the trained neural network 24A.

Then, the radiation image processing of deriving the estimation results of the body thickness, the bone mineral density, and the muscle mass in the present embodiment will be described. FIG. 21 is a flowchart showing the radiation image processing performed in the present embodiment. Note that the simple radiation image G0, which is a processing target, is acquired by the imaging and stored in the storage 13. In a case in which an instruction for starting the processing is input from the input device 15, the image acquisition unit 21 acquires the simple radiation image G0 from the storage 13 (step ST11). Then, the estimation unit 24 derives the estimation results of the body thickness, the bone mineral density, and the muscle mass from the simple radiation image G0 (step ST12). Moreover, the display controller 25 displays the estimation result on the display 14 together with the simple radiation image G0 (step ST13), and terminates the processing.

As described above, in the present embodiment, the trained neural network 24A is constructed by using the teacher data 40 consisting of the learning data 41 including the standard image 41A, the radiation energy characteristic 41B, the object characteristic 41C, and the imaging condition 41D, and the correct answer data 42 including the body thickness 42A, the bone mineral density 42B, and the muscle mass 42C derived from the radiation image of the subject by using the standard image 41A, the radiation energy characteristic 41B, the object characteristic 41C, and the imaging condition 41D. Moreover, by using the trained neural network 24A, the estimation results of the body thickness, the bone mineral density, and the muscle mass for the simple radiation image G0 acquired by imaging the subject H, which is a target, are derived.

Here, in the present embodiment, in a case in which the body thickness 42A, the bone mineral density 42B, and the muscle mass 42C as the correct answer data 42 are derived, by using the energy characteristic of the radiation in the imaging apparatus 1, the relationship between the thickness of the standard object 70 and the radiation attenuation coefficient, which reflects the influence of the beam hardening of the object, such as the top plate 3A and the grid 4, interposed between the subject H and the first and second radiation detectors 5 and 6 is derived, the primary ray component and the scattered ray component depending on the thickness of the standard object 70 included in the standard image K0 are derived based on the derived relationship, and the scattered ray model representing the relationship between the thickness of the standard object 70 and the ratio of the scattered ray component to the primary ray component is derived. Moreover, by removing the scattered ray component using the derived scattered ray model and by using the first and second radiation images G1 and G2 from which the scattered ray component is removed, the body thickness, the bone mineral density, and the muscle mass are derived in consideration of the energy characteristic of the radiation emitted to the subject H and the object interposed between the subject and the radiation detector.

Therefore, according to the present embodiment, by using the constructed trained neural network 24A, the body thickness, the bone mineral density, and the muscle mass of the subject H, which is a target, can be estimated with high accuracy in consideration of the energy characteristic of the radiation emitted to the subject H and the object interposed between the subject H and the radiation detector.

Note that, in the embodiment described above, the trained neural network 24A is constructed to output the body thickness, the bone mineral density, and the muscle mass by inputting the simple radiation image G0 of the subject H, the present disclosure is not limited to this. The trained neural network 24A may be constructed to output the body thickness, the bone mineral density, and the muscle mass by inputting the first and second radiation images G1 and G2 having different energy distributions for the subject H, which is a target.

In addition, in the embodiment described above, the trained neural network 24A is constructed to output the body thickness, the bone mineral density, and the muscle mass, the present disclosure is not limited to this. The trained neural network 24A may be constructed to output any one of the body thickness, the bone mineral density, or the muscle mass, or a combination of two of the body thickness, the bone mineral density, and the muscle mass. In this case, the teacher data 40 including any one of the body thickness, the bone mineral density, or the muscle mass, or a combination of two of the body thickness, the bone mineral density, and the muscle mass as the correct answer data 42 need only be prepared. The trained neural network 24A constructed in this way outputs any one of the body thickness, the bone mineral density, or the muscle mass, or a combination of two of the body thickness, the bone mineral density, and the muscle mass by inputting the simple radiation image G0, or the first and second radiation images G1 and G2.

In addition, in the embodiment described above, the object interposed between the subject H and the radiation detectors 5 and 6 is the top plate 3A and the grid 4, but the present disclosure is not limited to this. In a case in which the grid 4 is not used, the object interposed between the subject H and the radiation detectors 5 and 6 is only the top plate 3A. In addition, in a case in which the subject H is imaged in a standing position instead of a lying down position, only the grid 4 may be used without using the top plate 3A. In this case, the object interposed between the subject H and the radiation detectors 5 and 6 is only the grid 4. In this way, in a case in which the object interposed between the subject H and the radiation detectors 5 and 6 is only the top plate 3A or only the grid 4, the relationship between the thickness of the standard object 70 and the radiation attenuation coefficient, which reflects the influence of the radiation attenuation coefficient of only the top plate 3A or the beam hardening of only the grid 4, need only be derived to derive the correct answer data 42.

In addition, in the embodiment described above, in a case in which the muscle mass 42C is derived as the correct answer data 42, by performing the energy subtraction processing, the muscle image Gm obtained by extracting the muscle in the soft tissue of the subject H may be derived from the first and second radiation images G1 and G2 which are subjected to the scattered ray removal processing. In a case in which the muscle image Gm is derived, the subtraction unit 68 need only perform weighting subtraction between the corresponding pixels with respect to the first and second radiation images G1 and G2 as shown in Expression (26) to generate the muscle image Gm in which the muscle of the subject H included in each of the radiation images G1 and G2 is extracted. In Expression (26), β3 is a weighting coefficient, and is set as a value capable of extracting the muscle of the subject H included in each of the radiation images G1 and G2 by Expression (26) based on the radiation attenuation coefficients of the fat and the muscle.

$$Gm(x,y)=G1(x,y)-\beta 3\times G2(x,y) \tag{26}$$

In addition, in the embodiment described above, the first and second radiation images G1 and G2 are acquired by the one-shot method, but the present disclosure is not limited to this. The first and second radiation images G1 and G2 may be acquired by a so-called two-shot method for performing imaging twice. In a case of the two-shot method, a position of the subject H included in the first radiation image G1 and the second radiation image G2 may shift due to a body movement of the subject H. Therefore, in the first radiation image G1 and the second radiation image G2, it is preferable to perform the processing according to the present embodiment after registration of the subject is performed. As registration processing, for example, a method disclosed in JP2011-255060A can be used. In the method disclosed in JP2011-255060A, for each of the first and second radiation images G1 and G2, a plurality of first band images and a plurality of second band images representing structures having different frequency bands are generated, a misregistration amount of the positions corresponding to each other in the first band image and the second band image of the corresponding frequency band is acquired, and the registration of the first radiation image G1 and the second radiation image G2 is performed based on the misregistration amount.

In addition, in the embodiment described above, the learning processing and the radiation image processing are performed by using the radiation image of the subject acquired in the system that images the subject H by using the first and second radiation detectors 5 and 6. However, it is needless to say that the technology of the present disclosure can also be applied to the system that acquires the radiation image of the subject by using an accumulative phosphor sheet instead of the radiation detector. In this case, the simple radiation image G0 need only be acquired by irradiating one accumulative phosphor sheets with the radiation transmitted through the subject H, accumulating and recording radiation image information of the subject H in the accumulative phosphor sheets, and photoelectrically reading the radiation image information from the accumulative phosphor sheets. The first and second radiation images G1 and G2 need only be acquired by stacking two accumulative phosphor sheets, emitting the radiation transmitted through the subject H, accumulating and recording radiation image information of the subject H in each of the accumulative phosphor sheets, and photoelectrically reading the radiation image information from each of the accumulative phosphor sheets. Note that the two-shot method may also be used in a case in which the first and second radiation images G1 and G2 are acquired by using the accumulative phosphor sheet.

In addition, the radiation in the embodiment described above is not particularly limited, and α-rays or γ-rays can be used in addition to X-rays.

In addition, in the embodiment described above, various processors shown below can be used as the hardware structures of processing units that execute various pieces of processing, such as the image acquisition unit 21, the information acquisition unit 22, the learning unit 23, the estimation unit 24, and the display controller 25. As described above, the various processors include, in addition to the CPU that is a general-purpose processor which executes software (program) and functions as various processing units, a programmable logic device (PLD) that is a processor whose circuit configuration can be changed after manufacture, such as a field programmable gate array (FPGA), and a dedicated electric circuit that is a processor having a circuit configuration which is designed for exclusive use in order to execute a specific processing, such as an application specific integrated circuit (ASIC).

One processing unit may be configured by one of these various processors, or may be a combination of two or more processors of the same type or different types (for example, a combination of a plurality of FPGAs or a combination of the CPU and the FPGA). In addition, a plurality of the processing units may be configured by one processor.

As an example of configuring the plurality of processing units by one processor, first, as represented by a computer, such as a client and a server, there is an aspect in which one processor is configured by a combination of one or more CPUs and software and this processor functions as a plurality of processing units. Second, as represented by a system on chip (SoC) or the like, there is an aspect of using a processor that realizes the function of the entire system including the plurality of processing units by one integrated circuit (IC) chip. In this way, as the hardware structure, the various processing units are configured by using one or more of the various processors described above.

Moreover, as the hardware structures of these various processors, more specifically, it is possible to use an electrical circuit (circuitry) in which circuit elements, such as semiconductor elements, are combined.

In the following, the supplementary notes of the present disclosure are described.

Supplementary Note 1

A scattered ray model derivation device comprising at least one processor, in which the processor acquires at least one standard image representing a standard object having different thicknesses, the at least one standard image being obtained by imaging the standard object by radiation in a state in which an object is interposed between the standard object and a radiation detector, derives a relationship between the thickness of the standard object and a radiation attenuation coefficient of the standard object, which corresponds to an energy characteristic of the radiation, the relationship reflecting an influence of beam hardening by the standard object and the object, derives a primary ray component corresponding to the thickness of the standard object included in the standard image based on the relationship between the thickness of the standard object and the radiation attenuation coefficient of the standard object, derives a scattered ray component corresponding to the thickness of the standard object included in the standard image based on a difference between the standard image and the primary ray component, and derives a scattered ray model representing a relationship between the thickness of the standard object and a ratio of the scattered ray component to the primary ray component.

Supplementary Note 2

The scattered ray model derivation device according to Supplementary Note 1, in which the processor derives the relationship between the thickness of the standard object and the radiation attenuation coefficient of the standard object based on the energy characteristic of the radiation, the radiation attenuation coefficient of the standard object which corresponds to the energy characteristic, the thickness of the standard object, a radiation attenuation coefficient of the object which corresponds to the energy characteristic, and a thickness of the object.

Supplementary Note 3

The scattered ray model derivation device according to Supplementary Note 1, in which the processor derives the relationship between the thickness of the standard object and the radiation attenuation coefficient of the standard object based on the energy characteristic of the radiation, the radiation attenuation coefficient of the standard object which corresponds to the energy characteristic, the thickness of the standard object, a radiation attenuation coefficient of the object which corresponds to the energy characteristic, and the energy characteristics of the radiation before and after being transmitted through the object.

Supplementary Note 4

The scattered ray model derivation device according to any one of Supplementary Notes 1 to 3, in which the processor derives the relationship between the thickness of the standard object and the radiation attenuation coefficient of the standard object for a thickness that is not present in the standard object by interpolating the relationship between the thickness of the standard object and the radiation attenuation coefficient of the standard object for a thickness that is present in the standard object, derives the primary ray component for the thickness that is not present in the standard object by interpolating the primary ray component for the thickness that is present in the standard object, derives the scattered ray component for the thickness that is not present in the standard object by interpolating the scattered ray component for the thickness that is present in the standard object, and derives the scattered ray model for the thickness that is not present in the standard object by interpolating the scattered ray model for the thickness that is present in the standard object.

Supplementary Note 5

The scattered ray model derivation device according to any one of Supplementary Notes 1 to 4, in which the object is at least one of a top plate of an imaging table on which a subject is placed in an imaging apparatus or a scattered ray removal grid for removing the scattered ray component from the radiation transmitted through the subject.

Supplementary Note 6

A radiation image processing device comprising at least one processor, in which the processor acquires at least one radiation image of a subject, acquires a body thickness distribution of the subject, and derives at least one processed radiation image by removing a scattered ray component included in the radiation image by using the scattered ray model derived by the scattered ray model derivation device according to any one of Supplementary Notes 1 to 5 and the body thickness distribution of the subject.

Supplementary Note 7

The radiation image processing device according to Supplementary Note 6, in which the processor derives a primary ray component included in the at least one radiation image by using the scattered ray model and the body thickness distribution of the subject, and derives the at least one processed radiation image by updating the body thickness distribution, the scattered ray component, and the primary ray component until a difference between the primary ray component and the processed radiation image satisfies a predetermined condition.

Supplementary Note 8

The radiation image processing device according to Supplementary Note 6 or 7, in which the radiation image of the subject is a first radiation image and a second radiation image based on radiation having different energy distributions, which is transmitted through the subject including a bone part and a soft part, and the processor derives a first processed radiation image and a second processed radiation image for the first radiation image and the second radiation image, respectively, by removing the scattered ray component from each of the first radiation image and the second radiation image by using the scattered ray model, and derives a composition of the subject from the first processed radiation image and the second processed radiation image.

Supplementary Note 9

The radiation image processing device according to Supplementary Note 8, in which the processor derives a bone part image obtained by extracting the bone part of the subject from the first processed radiation image and the second processed radiation image, and derives a bone mineral density as the composition for each pixel of a bone region of the bone part image based on a pixel value of the bone part image.

Supplementary Note 10

The radiation image processing device according to Supplementary Note 9, in which the processor derives the bone mineral density for each pixel of the bone region by correcting the pixel value of the bone part image by a correction coefficient derived based on a radiation attenuation coefficient of the bone part.

Supplementary Note 11

The radiation image processing device according to Supplementary Note 10, in which the correction coefficient is also derived based on a radiation attenuation coefficient of an object interposed between the subject and a radiation detector that acquires the first radiation image and the second radiation image.

Supplementary Note 12

The radiation image processing device according to Supplementary Note 8, in which the processor derives a muscle image obtained by extracting a muscle of the subject from the first processed radiation image and the second processed radiation image, and derives a muscle mass as the composition for each pixel of the muscle image based on a pixel value of the muscle image.

Supplementary Note 13

The radiation image processing device according to Supplementary Note 12, in which the processor derives a soft part image obtained by extracting a soft part of the subject from the first processed radiation image and the second processed radiation image, derives the muscle image from the soft part image, and derives the muscle mass for each pixel of the muscle image by correcting the pixel value of the muscle image by a correction coefficient derived based on a radiation attenuation coefficient of the muscle.

Supplementary Note 14

The radiation image processing device according to Supplementary Note 13, in which the correction coefficient is also derived based on a radiation attenuation coefficient of an object interposed between the subject and a radiation detector that acquires the first radiation image and the second radiation image.

Supplementary Note 15

The radiation image processing device according to any one of Supplementary Notes 8 to 14, in which the processor displays the composition on a display.

Supplementary Note 16

A scattered ray model derivation method comprising acquiring at least one standard image representing a standard object having different thicknesses, the at least one standard image being obtained by imaging the standard object by radiation in a state in which an object is interposed between the standard object and a radiation detector, deriving a relationship between the thickness of the standard object and a radiation attenuation coefficient of the standard object, which corresponds to an energy characteristic of the radiation, the relationship reflecting an influence of beam hardening by the standard object and the object, deriving a primary ray component corresponding to the thickness of the standard object included in the standard image based on the relationship between the thickness of the standard object and the radiation attenuation coefficient of the standard object, deriving a scattered ray component corresponding to the thickness of the standard object included in the standard image based on a difference between the standard image and the primary ray component, and deriving a scattered ray model representing a relationship between the thickness of the standard object and a ratio of the scattered ray component to the primary ray component.

Supplementary Note 17

A radiation image processing method comprising acquiring at least one radiation image of a subject, acquiring a body thickness distribution of the subject, and deriving at least one processed radiation image by removing a scattered ray component included in the radiation image by using the scattered ray model derived by the scattered ray model derivation device according to any one of Supplementary Notes 1 to 5 and the body thickness distribution of the subject.

Supplementary Note 18

A scattered ray model derivation program causing a computer to execute a procedure of acquiring at least one standard image representing a standard object having different thicknesses, the at least one standard image being obtained by imaging the standard object by radiation in a state in which an object is interposed between the standard object and a radiation detector, a procedure of deriving a relationship between the thickness of the standard object and a radiation attenuation coefficient of the standard object, which corresponds to an energy characteristic of the radiation, the relationship reflecting an influence of beam hardening by the standard object and the object, a procedure of deriving a primary ray component corresponding to the thickness of the standard object included in the standard image based on the relationship between the thickness of the standard object and the radiation attenuation coefficient of the standard object, a procedure of deriving a scattered ray component corresponding to the thickness of the standard object included in the standard image based on a difference between the standard image and the primary ray component, and a procedure of deriving a scattered ray model representing a relationship between the thickness of the standard object and a ratio of the scattered ray component to the primary ray component.

Supplementary Note 19

A radiation image processing program causing a computer to execute a procedure of acquiring at least one radiation image of a subject, a procedure of acquiring a body thickness distribution of the subject, and a procedure of deriving at least one processed radiation image by removing a scattered ray component included in the radiation image by using the scattered ray model derived by the scattered ray model derivation device according to any one of Supplementary Notes 1 to 5 and the body thickness distribution of the subject.

What is claimed is:

1. A learning device comprising:
    at least one processor,
    wherein the at least one processor acquires teacher data consisting of learning data and correct answer data, and constructs, by subjecting a neural network to machine learning using the teacher data, a trained neural network,
    wherein the trained neural network is constructed so as to output at least one of a composition of a target subject or a body thickness of the target subject in a case in which at least one target radiation image of the target subject is input, wherein the learning data includes
- a standard image acquired by irradiating a standard object of which a thickness and a material are known with radiation in a state in which an object is interposed between the standard object and a radiation detector,
- an energy characteristic of the radiation,
- a thickness and a material of the object, and
- an imaging condition in a case in which the standard image is acquired, and wherein the correct answer data includes at least one of a composition or a body thickness of a subject derived from at least one radiation image for deriving the correct answer data, in which the subject is included and which is different from the target radiation image, by using the standard image, the energy characteristic of the radiation, the thickness and the material of the object, and the imaging condition.

2. The learning device according to claim 1,
wherein the object is at least one of a top plate of an imaging table in an imaging apparatus or a scattered ray removal grid for removing a scattered ray component from the radiation irradiated to the radiation detector.

3. The learning device according to claim 1,
wherein the target radiation image is a radiation image based on radiation transmitted through the target subject including a bone part and a soft part.

4. The learning device according to claim 1,
wherein the target radiation image is a first radiation image and a second radiation image based on radiation having different energy distributions transmitted through the target subject including a bone part and a soft part.

5. The learning device according to claim 1,
wherein the composition of the subject and the composition of the target subject are at least one of a bone mineral density or a muscle mass.

6. A radiation image processing device comprising:
at least one processor,
wherein the at least one processor
   acquires at least one target radiation image of a target subject, and
   derives an estimation result of at least one of a composition of the target subject or a body thickness of the target subject by using a trained neural network and the target radiation image,
wherein the trained neural network is constructed by subjecting a neural network to machine learning using teacher data consisting of learning data and correct answer data, so that the trained neural network outputs at least one of a composition of a target subject or a body thickness of the target subject in a case in which at least one target radiation image of the target subject is input,
wherein the learning data includes
- a standard image acquired by irradiating a standard object of which a thickness and a material are known with radiation in a state in which an object is interposed between the standard object and a radiation detector,
- an energy characteristic of the radiation,
- a thickness and a material of the object, and
- an imaging condition in a case in which the standard image is acquired, and wherein the correct answer data includes at least one of a composition or a body thickness of a subject derived from at least one radiation image for deriving the correct answer data, in which the subject is included and which is different from the target radiation image, by using the standard image, the energy characteristic of the radiation, the thickness and the material of the object, and the imaging condition.

7. The radiation image processing device according to claim 6,
wherein the target radiation image is a radiation image based on radiation transmitted through the target subject including a bone part and a soft part.

8. The radiation image processing device according to claim 6,
wherein the target radiation image is a first radiation image and a second radiation image based on radiation having different energy distributions transmitted through the target subject including a bone part and a soft part.

9. The radiation image processing device according to claim 6,
wherein the composition of the target subject is at least one of a bone mineral density or a muscle mass.

10. A learning method comprising:
acquiring teacher data consisting of learning data and correct answer data, and
constructing, by subjecting a neural network to machine learning using the teacher data, a trained neural network,
wherein the trained neural network is constructed so as to output at least one of a composition of a target subject or a body thickness of the target subject in a case in which at least one target radiation image of the target subject is input,
wherein the learning data includes
- a standard image acquired by irradiating a standard object of which a thickness and a material are known with radiation in a state in which an object is interposed between the standard object and a radiation detector,
- an energy characteristic of the radiation,
- a thickness and a material of the object, and
- an imaging condition in a case in which the standard image is acquired, and wherein the correct answer data includes at least one of a composition or a body thickness of a subject derived from at least one radiation image for deriving the correct answer data, in which the subject is included and which is different from the target radiation image, by using the standard image, the energy characteristic of the radiation, the thickness and the material of the object, and the imaging condition.

11. A radiation image processing method comprising:
acquiring at least one target radiation image of a target subject; and
deriving an estimation result of at least one of a composition of the target subject or a body thickness of the target subject by using a trained neural network and the target radiation image,
wherein the trained neural network is constructed by subjecting a neural network to machine learning using teacher data consisting of learning data and correct answer data, so that the trained neural network outputs at least one of a composition of a target subject or a body thickness of the target subject in a case in which at least one target radiation image of the target subject is input, wherein the learning data includes
- a standard image acquired by irradiating a standard object of which a thickness and a material are known with radiation in a state in which an object is interposed between the standard object and a radiation detector,
- an energy characteristic of the radiation,
- a thickness and a material of the object, and
- an imaging condition in a case in which the standard image is acquired, and wherein the correct answer data includes at least one of a composition or a body thickness of a subject derived from at least one radiation image for deriving the correct answer data, in which the subject is included and which is different from the target radiation image, by using the standard image, the energy characteristic of the radiation, the thickness and the material of the object, and the imaging condition.

12. A non-transitory computer-readable storage medium that stores a learning program causing a computer to execute a procedure of acquiring teacher data consisting of learning data and correct answer data, and
- a procedure of constructing, by subjecting a neural network to machine learning using the teacher data, a trained neural network, wherein the trained neural network is constructed so as to output at least one of a composition of a target subject or a body thickness of the target subject in a case in which at least one target radiation image of the target subject is input, wherein the learning data includes
- a standard image acquired by irradiating a standard object of which a thickness and a material are known with radiation in a state in which an object is interposed between the standard object and a radiation detector,
- an energy characteristic of the radiation,
- a thickness and a material of the object, and
- an imaging condition in a case in which the standard image is acquired, and wherein the correct answer data includes at least one of a composition or a body thickness of a subject derived from at least one radiation image for deriving the correct answer data, in which the subject is included and which is different from the target radiation image, by using the standard image, the energy characteristic of the radiation, the thickness and the material of the object, and the imaging condition.

13. A non-transitory computer-readable storage medium that stores a radiation image processing program causing a computer to execute:
- a procedure of acquiring at least one target radiation image of a target subject; and
- a procedure of deriving an estimation result of at least one of a composition of the target subject or a body thickness of the target subject by using a trained neural network and the target radiation image, wherein the trained neural network is constructed by subjecting a neural network to machine learning using teacher data consisting of learning data and correct answer data, so that the trained neural network outputs at least one of a composition of a target subject or a body thickness of the target subject in a case in which at least one target radiation image of the target subject is input, wherein the learning data includes
- a standard image acquired by irradiating a standard object of which a thickness and a material are known with radiation in a state in which an object is interposed between the standard object and a radiation detector,
- an energy characteristic of the radiation,
- a thickness and a material of the object, and
- an imaging condition in a case in which the standard image is acquired, and wherein the correct answer data includes at least one of a composition or a body thickness of a subject derived from at least one radiation image for deriving the correct answer data, in which the subject is included and which is different from the target radiation image, by using the standard image, the energy characteristic of the radiation, the thickness and the material of the object, and the imaging condition.

* * * * *